US008338190B2

(12) United States Patent
Hoey et al.

(10) Patent No.: US 8,338,190 B2

(45) Date of Patent: Dec. 25, 2012

(54) **TYPE IV SECRETION SYSTEM PROTEINS IN SERO-DETECTION OF *ANAPLASMA PHAGOCYTOPHILUM***

(75) Inventors: John G. Hoey, Framingham, MA (US); Denise P. Dimitrov, Hamilton, NJ (US); Lisa P. Huang, Princeton, NJ (US); Martin E. Adelson, East Windsor, NJ (US); Eli Mordechai, Robbinsville, NJ (US)

(73) Assignee: Medical Diagnostic Laboratories, LLC, Hamilton, NJ (US)

(*) Notice: Subject to any disclaimer, the term of this patent is extended or adjusted under 35 U.S.C. 154(b) by 0 days.

(21) Appl. No.: 13/561,587

(22) Filed: Jul. 30, 2012

(65) Prior Publication Data

US 2012/0288882 A1 Nov. 15, 2012

Related U.S. Application Data

(62) Division of application No. 12/658,268, filed on Feb. 9, 2010.

(60) Provisional application No. 61/208,745, filed on Feb. 27, 2009.

(51) Int. Cl.
*G01N 33/543* (2006.01)

(52) U.S. Cl. .......................................................... 436/518

(58) Field of Classification Search ......................... None
See application file for complete search history.

(56) References Cited

U.S. PATENT DOCUMENTS 6,964,855 B2 * 11/2005 O'Connor et al. ........... 435/7.32

OTHER PUBLICATIONS

Ohashi et al. (Infect. Immun., 70:2128-2138, 2002).*
Hotopp et al. (PLOS Genetics, 2:e1-21, 2006).*

* cited by examiner

*Primary Examiner* — Brian J Gangle
(74) *Attorney, Agent, or Firm* — Siu K. Lo, Esq.

(57) ABSTRACT

Disclosed are two (2) proteins in the Type IV Secretion System (TIVSS) in *Anaplasma phagocytophilum* (namely, virB10 and virB11) useful in the ELISA detection of *Anaplasma* pathogen. The recombinant expression of virB10 and virB11 and their use as kits for ELISA are also disclosed.

18 Claims, 21 Drawing Sheets

Type IV Secretion System in *Agrobacterium tumefaciens*

**Ek/LIC PCR Amplification of *Anaplasma* Genes for Expression in *E. coli***

M1: DNA Ladder (0.2-10 Kb)
M2: DNA Ladder (0.1-1.0 Kb)
1: SuccDEH
2: TIVSS virB3
3: TIVSS virB4
4: TIVSS virB6 (2,541 bp)
5: TIVSS virB8
6: (-) 1
7: (-) 2
8: (-) 3
9: (-) 4
10: (-) 5
11: TIVSS virB9-1 (817 bp)
12: TIVSS virB9.2
13: TIVSS virB10 (1,305 bp)
14: TIVSS virB11 (999 bp)
15: TIVSS virD4
16: (-) 6
17: (-) 7
18: (-) 8
19: (-) 9
20: (-) 10

Anaplasma Clones for Expression in *E. coli* (post-PCR clean-up)

Figure 8

TIVSS virB9

Nucleotide Sequence (SEQ ID No. 25)

```
  1 ATGATGAATT TCTATAAAAA TTTTTATGTT GCTTTGGTAA CGGCTTTCGC
 51 GCTGTTCTCT ATGAGTAAAG CATGCTTTGC CAGCACAAAT ATTGGCGTAC
101 CAGTTTCTGT AGATAGTAGA ATAAAGACAT TTGTCTACAG TCAGAATGAG
151 GTTTTTCCGG TTGTGTTCAA CTATGGCTAT CATTCCTACA TAGAATTCTC
201 GCAAGGTGAG ACGGTGCGAG TTATGGCTTT AGGAGATAAT GCAAATTGGA
251 AGATAAGGCC GGTGGACAAC AAGTTATACG TCATGCCCTT GGAAAAAGAG
301 GGGCACACTA ATATGCTCAT AGAAACGAGT AAGGGGCGGA GTTACGCTTT
351 TGATTTGATA TCGACTGCGA TTCCTCTGAG TGGAGGTGCT GCATCTAGTA
401 TTAACAAGTT GGGAAAGACT AATTCTGCAT TAGCAGACTT AGCTTATGTA
451 GTGCGTTTTT ACTATCCGCA GAGTGATAGA AATTTTGATA TCATGGGACA
501 GAAACTTGAG ATATCTCCTC CTAGCCTGGC TAGCAGTTTA GATGCTGATG
551 ATGTGGAAAT AGAGCCAAAT GCCACTAGAA CCAACTATAT GTTTACTGGT
601 GGAAGTGCTC ACGTTTCTCT AGCTCCTACG CAGGCTTTTG ATGATGGATA
651 TCTGACATAC TTTCAGTTTG GTAAAAATAA CAAAGAAATT CCCAAAATCT
701 ACGTTGTGAA GAAGGATGGA AAAAAAGTTC CATGTAAAAT GCTGCTTCTT
751 AGGGACTATG TAATAGTTGA GGGGGTGCAT GAGCTGTTTT ACCTTGATTT
801 TGGTGATGGC AGGAGTGTAG AAGTTGTGAA TCAGGCTCTT AGTTAG
```

Deduced Amino Acid Sequence (SEQ ID No. 31)

```
MMNFYKNFYVALVTAFALFSMSKACFASTNIGVPVSVDSRIKTFVYSQNE 50
VFPVVFNYGYHSYIEFSQGETVRVMALGDNANWKIRPVDNKLYVMPLEKE 100
GHTNMLIETSKGRSYAFDLISTAIPLSGGAASSINKLGKTNSALADLAYV 150
VRFYYPQSDRNFDIMGQKLEISPPSLASSLDADDVEIEPNATRTNYMFTG 200
GSAHVSLAPTQAFDDGYLTYFQFGKNNKEIPKIYVVKKDGKKVPCKMLLL 250
RDYVIVEGVHELFYLDFGDGRSVEVVNQALS*
```

Figure 9

TIVSS virB10
Nucleotide Sequence (SEQ ID No. 26)

```
   1 ATGGCTGACG AAATAAGGGG TTCTAGCAGC GGGGAGAACA TTGAGGATAA
  51 TGTTAATGTA GTAGGTGTAG CAAAGAGTAA GAAGCTCTTT GTTATCATAG
 101 TGGTGCTGAT TGCTACTGGA CTTATGTACT ATTTTTTCTT CTTCAATAAG
 151 GAGTCTTCGG ATAATGAGGA AGATACTCAG ATTCCTCGTG TTATCGAAGA
 201 GAAGGAAGTA GAAAAATTGA GGAAGGATGC GGGAAGGCCG GCTCAGGAGA
 251 CTGCTCCTAG AATCTTGACG CCACCACCGA GGTTGCCTGA GTTGCCGCCG
 301 CTTGTAATGC CTACTGTACC TGATATTCCT GTGGTAACAA AATTGCTTAA
 351 GCCGCCTGTA GAGGAGGAGT TTGTTGAAGA GTATAACGTT CAAGAGGTTC
 401 CTTCACCAAT GGGTAATATT GCTCCTCCTG AACGCGAGGA GATATCTTTA
 451 CCTTTGCCGT ATAAGACGAT AACAACTGAG CAGCCGTCGT TTCTGGGGTA
 501 TGATAAAGAA AAAAGAGGAG CCCCTATGAT CGCATTTGGT GGCGGTGGTG
 551 GCGAAGCTGC TGGTAGTGAA TCCGGTGATG GTTCTGTTGG CGGGAAGGAA
 601 GATGCTCGGT TTACTGCGTG GCAAGGGTTA GAGGGTACTC AATCTCCTAG
 651 TGTTAGAGCG ACAAGAGTGG GGGATACGAG ATATATAATA CTGCAAGGTC
 701 ACATGATTGA TGCTGTTTTA GAGACAGCAA TAAACTCGGA TATTTCAGGG
 751 GTGCTCAGGG CTGTGGTATC CAGAGATGTA TATGCTTCTT CTGGAGATGC
 801 GGTTGTAATA CCGAAGGGGT CTAGGCTTAT TGGTAGTTAT TTCTTTGATT
 851 CTGCTGGTAA CAATGTAAGG GTTGATGTTA ATTGGTCCAG GGTCATTTTA
 901 CCTCATGGCG TTGATATACA GATAGCGTCT AGTGGAACTG ATGAACTAGG
 951 AAGAAATGGT ATTTCTGGTG TTGTAGATAA TAAAGTGGGC TCCATATTGA
1001 CCTCTACTAT CTTTTTGGCG GGTATATCTT TGGGGACAGC TTATGTGACC
1051 GAGCAGATAC CGTCGTTGCG GACTGAGACT GTTAAGGTTG AGACTCCTGC
1101 GGATGGTAAA GACGGGAAGA AAACTACTTC ATCATCTCTT TCAACAAAGA
1151 TAGTTTCTGA TGCTATTAAG GATTTCTCTG ACTCTATGAA AGAGATTGTG
1201 AATAAGTATT CTAATAGGAC TCCGACTGTC TATGTAGATC AGGGTACTGT
1251 GATGAAGGTA TTTGTGAATC AGGACGTAGT ATTTCCTCGT GATGCGGTGA
1301 GGTAG
```

Deduced Amino Acid Sequence (SEQ ID No. 32)

```
MADEIRGSSSGENIEDNVNVVGVAKSKKLFVIIVVLIATGLMYYFFFFNK 50
ESSDNEEDTQIPRVIEEKEVEKLRKDAGRPAQETAPRILTPPPRLPELPP 100
LVMPTVPDIPVVTKLLKPPVEEEFVEEYNVQEVPSPMGNIAPPEREEISL 150
PLPYKTITTEQPSFLGYDKEKRGAPMIAFGGGGGEAAGSESGDGSVGGKE 200
DARFTAWQGLEGTQSPSVRATRVGDTRYIILQGHMIDAVLETAINSDISG 250
VLRAVVSRDVYASSGDAVVIPKGSRLIGSYFFDSAGNNVRVDVNWSRVIL 300
PHGVDIQIASSGTDELGRNGISGVVDNKVGSILTSTIFLAGISLGTAYVT 350
EQIPSLRTETVKVETPADGKDGKKTTSSSLSTKIVSDAIKDFSDSMKEIV 400
NKYSNRTPTVYVDQGTVMKVFVNQDVVFPRDAVR*
```

Figure 10

TIVSS virB11

Nucleotide Sequence (SEQ ID No. 27)

```
  1 ATGACTGGGG GTGGTGCAGC TTTAGAAACT TATCTTGAAC CGCTTCGGGA
 51 TATATTTGCT GAAGAAGGAG TAAATGAAAT ATCAATAAAT AACTCATGTG
101 AAGTATGGGT TGAAAATAGG GGAAATATTA GGTGCGAGCA TATTGCAGCA
151 TTGACGACTT CTCATCTCAG GGGGTTAGGG CGTCTTATTG CTCAGGCTAC
201 GGAGCAAAAG TTAAGTGAGG AAACGCCACT GCTTTCTGCG TCTTTACCCA
251 ACGGGTTTCG TGTACAGGTA GTTTTTCCTC CGGCATGTGA GGGTGATAAG
301 ATAGTGATGT CGATTCGTAA GCCTTCTGCG ATGCAGTTGT CGCTTGATGA
351 TTATGAAAAA ATGGGGGCAT TTTCTCATGT TGCTCAGCAG AATGACAAGC
401 TCAGAGATGA AAATAGCGAA TTAGGTGAGT TGCTATCTAA GGGTAAAATA
451 AAGGAATTTT TAGAAACGGC GGTACAAAAA AAGAAGAATA TAATTGTGAG
501 TGGTGGTACC TCTACAGGGA AGACTACATT TACTAACGCT GCCTTGAGAG
551 CTATACCTTT AGAAGAGAGG ATTATTACTG TTGAAGACTC GAGGGAAATT
601 GTCCTATCTC ATCCAAATCG CGTACATTTA CTTGCTTCTA AAGGTGGGCA
651 AGGTAGAGCA CGTGTTGGTA CGCAAGATTT GATCGAAGCA TGTCTTCGTC
701 TTCGTCCGGA TAGGATTATA GTGGGGGAGT TGAGGGGTGC TGAAGCCTTT
751 AGTTTTTTGA GGGCTATTAA TACTGGGCAT CCTGGATCTA TTTCTACGTT
801 GCACGCTGAT ACTCCAAGGA TGGCTATAGA GCAGTTAAAG CTTATGGTAA
851 TACAGGCAGG AACGGGATTA CCAGCAGATC AGATTGTGAA TTACATAATG
901 AATATTGTGG ATGTGATAGT GCAGCTGAAG AGGAGCTCTG GTGGAGTGCG
951 CCATGTTTCA GACATTTTGT TCACTAAGTG TTCAGAGGGT AATAAGTAA
```

Deduced Amino Acid Sequence (SEQ ID No. 33)

```
MTGGGAALETYLEPLRDIFAEEGVNEISINNSCEVWVENRGNIRCEHIAA   50
LTTSHLRGLGRLIAQATEQKLSEETPLLSASLPNGFRVQVVFPPACEGDK  100
IVMSIRKPSAMQLSLDDYEKMGAFSHVAQQNDKLRDENSELGELLSKGKI  150
KEFLETAVQKKKNIIVSGGTSTGKTTFTNAALRAIPLEERIITVEDSREI  200
VLSHPNRVHLLASKGGQGRARVGTQDLIEACLRLRPDRIIVGELRGAEAF  250
SFLRAINTGHPGSISTLHADTPRMAIEQLKLMVIQAGTGLPADQIVNYIM  300
NIVDVIVQLKRSSGGVRHVSDILFTKCSEGNK*
```

Colony PCR of Transformants in NovaBlue *E. coli*:
(amplified with Ek/LIC primers)

TIVSS virB10

Colony PCR of Transformants in BL21 (DE3) *E. coli* for Expression:
(amplified with vector-specific primers)

IPTG Induction of TIVSS Proteins (Soluble vs. Inclusion Body)

Ni-NTA Purification of 6XHis-Tagged Recombinant TIVSS Protein

E1-E5: pH 5.9 Elution
E6-E10: pH 5.0 Elution
E11-E15: pH 4.5 Elution

IgM and IgG ELISAs for recombinant virB9 virB9 IgM ELISA

Sensitivity= 66.7%
Specificity= 85.7% virB9 IgG ELISA

Failed checkerboard testing virB9 IgM ELISA ROC Analysis

IgM and IgG ELISAs for recombinant virB10

Sensitivity= 71.4%
Specificity= 90.5%

Sensitivity= 52.4%
Specificity= 85.7%

Figure 18
IgM and IgG ELISAs for recombinant virB11
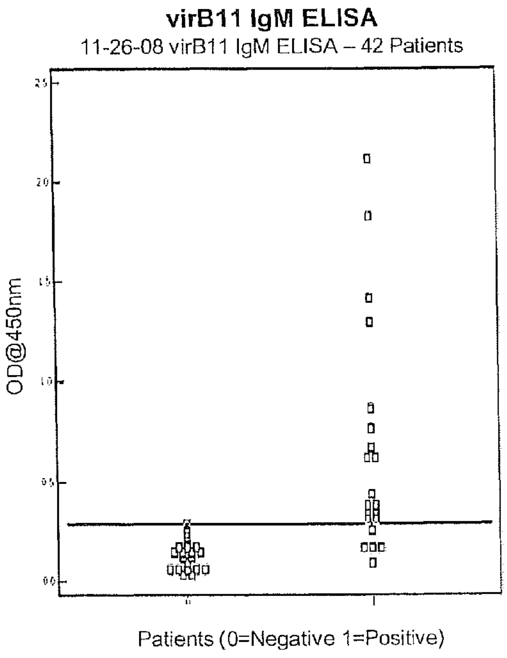
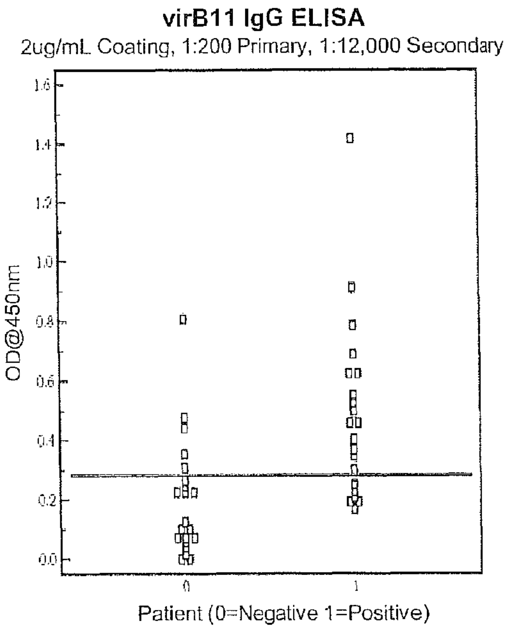
Sensitivity= 76.2%
Specificity= 95.2%
Sensitivity= 71.4%
Specificity= 76.2% virB11 ELISA ROC Analysis

TYPE IV SECRETION SYSTEM PROTEINS IN SERO-DETECTION OF *ANAPLASMA PHAGOCYTOPHILUM*

CROSS-REFERENCE TO RELATED APPLICATIONS

This application is a division of U.S. application Ser. No. 12/658,268 filed Feb. 9, 2010, which claims the benefit under 35 U.S.C.§119(e) to U.S. Provisional Application No. 61/208,745 filed Feb. 27, 2009, the contents of which are incorporated by reference herein in their entirety.

FIELD OF THE INVENTION

The present invention generally relates to the field of diagnostic assays for the detection of infectious agents in an animal, including humans. Particular embodiments disclosed herein encompass two (2) proteins within the Type IV Secretion System (TIVSS) (namely, virB10 and virB11) that are useful in the sero-detection of *Anaplasma phagocytophilum.*

BACKGROUND OF THE INVENTION

*Anaplasma phagocytophilum* is a tick-borne pathogen responsible for granulocytic anaplasmosis in humans (Bakken J. S., et al.: Human granulocytic ehrlichiosis in the upper Midwest United States. A new species emerging? *JAMA* 272: 212-218, 1994). There has been a steady rise in cases of *anaplasma* infections, alone or through co-infection with other tick-borne pathogens (Varde S., et al.: Prevalence of tick-borne pathogens in *Ixodes scapularis* in a rural New Jersey County. *Emerg. Infect. Dis.* 4: 97-99, 1998). Left unchecked, *anaplasma* infection can be a potentially fatal disease resulting from the targeting and replication of *Anaplasma phagocytophilum* within human neutrophils (Bakken J. S. et al.: *JAMA* 272: 212-218, 1994). *Anaplasma phagocytophilum* infection thus emerges as a significant healthcare concern.

Detection of *anaplasma* infection is crucial. Ideally, a diagnostic assay should be capable of detecting *anaplasma* infection at its earliest stages, when antibiotic treatment is most effective and beneficial. Traditional detection methods for *anaplasma* infection includes: (i) microscopic identification of morulae in granulocytes, (ii) PCR analysis using whole blood, (iii) isolation of the *anaplasma* bacterium from whole blood, and (iv) serological tests, particularly indirect immunofluorescence assay (IFA). Microscopic examination is tedious and prone to sampling error. PCR test is sensitive in detecting the tick-borne pathogen during the period of time when the pathogen is present in the blood of infected patients. IFA is most commonly used (Park, J., et al.: Detection of antibodies to *Anaplasma phagocytophilum* and *Ehrlichia chaffeensis* antigens in sera of Korean patients by western immunoblotting and indirect immunofluorescence assays. *Clinical and Diagnostic Laboratory Immunology* 10(6): 1059-1064, 2003), but this test often gives false positive results. Such results can be attributed in part to the use of whole-cell antigens because such proteins may be shared with other bacteria (Magnarelli, L. A., et al.: Use of recombinant antigens of *Borrelia burgdorferi* and *Anaplasma phagocytophilum* in enzyme-linked immunosorbent assays to detect antibodies in white-tailed deer. *J. Wildlife Dis.* 40(2): 249-258, 2004). When clinical symptoms are manifested or high and stable antibody titers to *Anaplasma phagocytophilum* are found in patient blood, it reaches a late infection stage and bypass the window of antibiotic treatment.

So far, there are only a few surface proteins on *anaplasma* pathogen that are used in diagnostic assay for immuno-responses (i.e., IgG and IgM responses). It is generally believed that outer membrane proteins in pathogens are target for eliciting an immuno-response because they may be the first to be exposed to immune cells of a host. Regarding the *Anaplasma phagocytophilum* species, U.S. Pat. No. 6,964,855 discloses the use of an outer membrane protein and its fragments in a detection assay. U.S. Pat. No. 7,304,139 discloses a major surface protein 5 (MSP5) and its use in a diagnostic test. The '139 patent discloses a few patient's reactivity towards MSP5 and it lacks any data relating sensitivity and specificity, let alone any IgG/IgM distinction. Zhi et al. discloses cloning and expression of an outer membrane protein of 44 kDa and its use in a Western immunoblot assay (*J. Clinical Microbiology* 36(6): 1666-1673, 1998). Both MSP5 and p44 are outer membrane proteins in *Anaplasma phagocytophilum.* To the best knowledge of the inventors, there is no report on using any intracellular protein as an antigenic protein, let alone it use in ELISA detection for *Anaplasma phagocytophilum.*

In *Agrobacterium tumefaciens*, TIVSS consists of twelve (12) protein components. virB5 and a part of virB2 are proteins located on the outer surface of the pathogen. On the other hand, the rest of the TIVSS in *Agrobacterium tumefaciens* reside within the pathogen (See, FIG. 1). TIVSS in *Agrobacterium tumefaciens* may represent a prototype for TIVSS in other species. The number of TIVSS protein components varies among various different species in the family. TIVSS in *Agrobacterium tumefaciens* is believed to form a conduit for transportation of macromolecules (such as proteins) across the cell membrane. *Anaplasma phagocytophilum* is a phylogenetically distant species. TIVSS in *Anaplasma phagocytophilum* consists of eight (8) protein components. And the manner by which TIVSS proteins assembly and their respective functions in *Anaplasma phagocytophilum* is presently unknown. Flabio R. Araujo et al. recently reported that sera of cattle infected with *Anaplasma marginale* (a phylogenetically distant species of *Anaplasma phagocytophilum*) can recognize recombinant virB9, virB10, and elongation factor-Tu (EF-Tu). To the best of the inventor's knowledge, there is no information exists regarding the cloning and recombinant expression of the *Anaplasma phagocytophilum* TIVSS protein components.

There is a continuing need in the discovery of a novel antigen present in *Anaplasma phagocytophilum* that may be useful in sero-detection of this pathogen. The present invention cures all the above-mentioned defects and provides a useful detection assay for *Anaplasma phagocytophilum* infection. Disclosed herein are the cloning, expression, purification, and use of two recombinant type IV secretion system (TIVSS) proteins virB10 and virB11 (rTIVSS virB10 and rTIVSS virB11). Particular embodiments include the development of a diagnostic ELISA test useful for detecting IgM/IgG antibody responses to *Anaplasma phagocytophilum.* The present assay discriminates between *Anaplasma phagocytophilum* IFA-positive and IFA-negative patient samples with high sensitivity (>70%) and specificity (>90%) values.

SUMMARY OF THE INVENTION

The present invention provides polypeptides of *Anaplasma phagocytophilum* that is useful in the detection of *Anaplasma phagocytophilum.* The present invention provides recombinant TIVSS polypeptides and methods of using these polypeptides in the detection of recent and/or ongoing infections with *Anaplasma phagocytophilum*, which can be useful in the diagnosis of human granulocytic anaplasmosis.

In one aspect, the present invention provides an isolated polypeptide having an amino acid sequence selected from the group consisting of SEQ ID NO: 32 and SEQ ID NO: 33. Preferably, the isolated polypeptides virB10 and virB11 have an amino acid sequence set forth in SEQ ID NO: 32 or SEQ ID NO: 33, respectively.

In another aspect, the present invention provides a composition comprising the isolated virB10 or virB11 polypeptides and a support. Preferably, the support may be polyethylene, polypropylene and glass. Preferably, the support is a microtiter well.

In another aspect, the present invention provides an isolated polynucleotide with nucleotide sequence set forth in SEQ ID NO: 26 or SEQ ID NO: 27.

In one aspect, the present invention provides a vector comprising the isolated polynucleotide of virB10 or virB11. The vector may be pET. The vector may further comprise a promoter of DNA transcription operably linked to the isolated polynucleotides of interest. The vector may further comprises a promoter of DNA transcription operably linked to the isolated isolated polynucleotides of interest. The vector may be pET, pENTR, or pCR®8/GW/TOPO®. The promoter may be a lac promoter, trp promoter or tac promoter.

In one aspect, the present invention provides a host cell comprising the vector. The host cell may be *E. coli* and the *E. coli* may include NovaBlue K12 strain or BL21 (DE3).

In one aspect, the present invention provides a method of producing an isolated polypeptide of virB10 or virB11 having an amino acid set forth in SEQ ID NO: 32 or SEQ ID NO: 33, respectively. The method comprises the steps of: (i) introducing the isolated virB10 or virB11 genes into a host cell; (ii) growing the host cell in a culture under suitable conditions to permit production of said isolated polypeptide; and (iii) isolating the isolated polypeptides of virB10 or virB11.

In one aspect, the present invention provides a method of detecting the presence of an antibody against *Anaplasma phagocytophilum* in a biological sample of a mammal, comprising: (i) immobilizing an isolated polypeptide of virB10 or virB11 onto a surface, the amino acid sequences of virB10 and virB11 are set forth in SEQ ID NO: 32 or SEQ ID NO: 33; (ii) contacting the isolated polypeptide with a patient's biological sample, under conditions that allow formation of an antibody-antigen complex between the immobilized polypeptide (antigen) and an antibody against *Anaplasma phagocytophilum*; and (iii) detecting the formation of the antibody-antigen complex; the detected antibody-antigen complex is indicative of the presence of said antibody against *Anaplasma phagocytophilum* in the biological sample. Preferably, the mammal is a human. ELISA test employs an IgG or IgM assay. Preferably, the ELISA has a sensitivity of at least >70%, and a specificity of at least >80%.

In another aspect, the present invention provides a method of diagnosing an infection of *Anaplasma phagocytophilum* in a mammal, comprising the steps of: (i) obtaining a biological sample from a mammal suspected of having an *Anaplasma phagocytophilum* infection; (ii) immobilizing an isolated polypeptide of virB10 or virB11 on to a surface, (iii) contacting the immobilized polypeptide with the biological sample, under conditions that allow formation of an antibody-antigen complex; and (iv) detecting said antibody-antigen complex. The detected antibody-antigen complex is indicative of the presence of said antibody against *Anaplasma phagocytophilum* in the biological sample. Preferably, the biological sample is whole blood, and the antibody is IgG or IgM.

In yet another aspect, the present invention provides an article of manufacture comprising a packaging material; and the isolated polypeptides of virB10 or virB11. The article of manufacture may further comprise an instruction for detecting the presence of antibody against *Anaplasma phagocytophilum.*

BRIEF DESCRIPTION OF THE DRAWINGS

FIG. 8 depicts the Nucleotide Sequence for TIVSS virB9 Gene in *Anaplasma phagocytophilum* (accession # YP_505897) (SEQ ID NO:25), and its deduced amino acid sequence of TIVSS virB10 protein (SEQ ID NO:31).

FIG. 9 depicts the Nucleotide Sequence for TIVSS virB10 Gene in *Anaplasma phagocytophilum* (accession # YP_505896) (SEQ ID NO:26), and its deduced amino acid sequence of TIVSS virB10 protein (SEQ ID NO:32).

FIG. 10 depicts the Nucleotide Sequence for TIVSS virB11 Gene in *Anaplasma phagocytophilum* (accession # YP_505895) (SEQ ID NO:27), and its deduced amino acid sequence of TIVSS virB10 protein (SEQ ID NO:33).

FIG. 18 depicts the IgM and IgG ELISA for Recombinant virB11 of *Anaplasma phagocytophilum.*

DETAILED DESCRIPTION OF THE INVENTION

Figure 1:
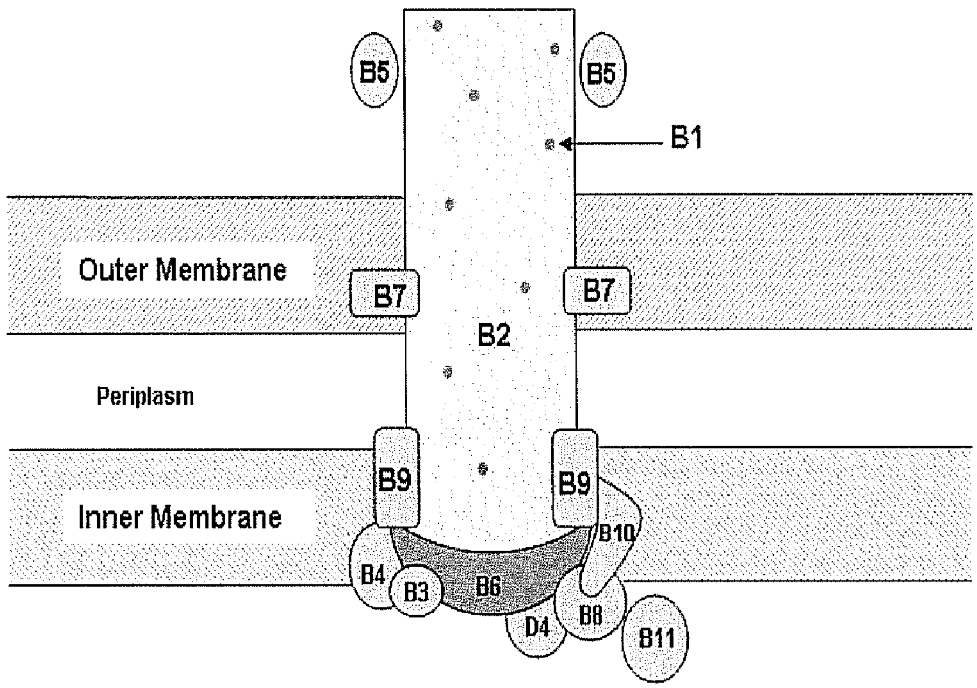
FIG. 1 schematically depicts the *Agrobacterium tumefaciens* Type IV Secretion System (TIVSS). Modified from KEGG: Kyoto Encyclopedia of Genes and Genomes (genome.ad.jp/dbgetbin/get_pathway?org_name=aph&mapno=03080).

The present invention can be better understood from the following description of preferred embodiments, taken in conjunction with the accompanying drawings. It should be apparent to those skilled in the art that the described embodiments of the present invention provided herein are merely exemplary and illustrative and not limiting.

DEFINITIONS

Various terms used throughout this specification shall have the definitions set out herein.

As used herein, "virB10" refers to a polypeptide having an amino acid sequence as set forth in SEQ ID NO: 26 (NCBI Accession No. YP_505896). The polypeptide represents the type IV secretion system virB10 protein present in *Anaplasma phagocytophilum* strain HZ. The virB10 polypeptide is shown by the present inventors to bind to antibodies that are present in *Anaplasma* patients' sera in an ELISA assay.

As used herein, "virB11" refers to a polypeptide having an amino acid sequence as set forth in SEQ ID NO: 27 (NCBI Accession No. YP_505895). The polypeptide represents the type IV secretion system virB11 protein present in *Anaplasma phagocytophilum* strain HZ. The virB11 polypeptide is shown by the present inventors to bind to antibodies that are present in *Anaplasma* patients' sera in an ELISA assay.

As used herein, the term "ELISA" refers to "Enzyme-Linked ImmunoSorbent Assay" and is a biochemical technique used in detecting the presence of antibody or antigen in a sample.

As used herein, the term "IFA" refers to immunofluorescence assay. "IFA sero-positive sera from a patient" refers to sera (obtained from a patient) that exhibit positive immunofluorescence staining towards cells that have been infected with *Anaplasma phagocytophilum*. "IFA sero-negative sera from a patient" refers to sera (obtained from a patient) that exhibit negligible immunofluorescence staining towards cells that have been infected with *Anaplasma phagocytophilum*.

As used herein, the terms "polypeptide," "peptide," or "protein" are used interchangeably.

As used herein, the term "recombinant polypeptide" refers to a polypeptide that is recombinantly expressed by a host cell via the use of a vector that has been modified by the introduction of a heterologous nucleic acid. For purposes of the present invention, these polypeptides are intended to encompass some polypeptide variations insofar as they retain the ability to bind to antibodies present in *Anaplasma* infected patients in an ELISA assay with comparable sensitivity and specificity. One of an ordinary skill in the art would appreciate that the polypeptide variations may include (i) conservative substitutions, (ii) substitution, (iii) addition, and (iv) deletion of amino acids. It would be further appreciated that a polypeptide variant having a sufficiently high % amino acid sequence identity (e.g., >95%), when exhibited similar antibody binding activity as to the parent polypeptide, is intended to be encompassed by the present invention.

As used herein, the term "% amino acid sequence identity" is defined as the percentage of amino acid residues that are identical to the amino acid residues in the TIVSS (e.g., virB10) polypeptide. Alignment for purposes of determining percent amino acid sequence identity can be achieved in various ways that are well within the skill in the art, for instance, using publicly available computer software such as BLAST, BLAST-2, ALIGN or Megalign (DNASTAR) software.

As used herein, the term "mammal" refers to any vertebrate of the class mammalia, having the body more or less covered with hair, nourishing the young with milk from the mammary glands, and, with the exception of the egg-laying monotremes, giving birth to live young. Preferably, the mammal is human.

As used herein, the term "primer" refers to a nucleotide sequence which can be extended by template-directed polymerization. For the purpose of this application, the term "nucleotide sequence" is intended to include DNA or modification thereof.

As used herein, the term "biological sample" may include but are not limited to blood (e.g., whole blood, blood serum, etc), cerebrospinal fluid, synovial fluid, and the like from a mammal such as a human or domestic animal. Extraction of nucleic acids from biological samples is known to those of skill in the art.

As used herein, the term "ROC" refers to Receiver Operating Characteristics Analysis. ROC analysis is a standard statistical tool for evaluation of clinical tests. ROC accesses the performance of the system in terms of "Sensitivity" and "1-Specificity" for each observed value of the discriminator variable assumed as decision threshold (i.e., cutoff value to differentiate between two groups of response). For ELISA, the cutoff value can be shifted over a range of observed values (i.e., $OD_{450}$ nm reading), and Sensitivity and 1-Specificity can be established for each of these values. The optimal pair of Sensitivity and Specificity is the point with the greatest distance in a Northwest direction.

The present invention provides recombinant and synthetic polypeptides that, when assayed in an ELISA assay, react to IFA sero-positive sera and do not react to IFA sero-negative sera from a patient infected with *Anaplasma phagogtophilum.*

Recombinant Polypeptides of TIVSS

The present invention specifically contemplates expression and preparation of recombinant and synthetic polypeptides, characterized by being capable of binding to antibodies present in IFA positive patient sera. In one embodiment, the present invention thus comprises the isolated nucleic acid having the nucleotide sequence set forth in FIG. 9 (SEQ ID NO: 26). The recombinant proteins of virB10 expressed by the nucleic acids described herein encompasses the protein set forth in FIG. 9 (SEQ ID NO: 32). The recombinant virB10 protein described herein possesses the ability to bind to antibodies present in IFA positive sera (and not IFA negative sera).

In another embodiment, the present invention thus comprises the isolated nucleic acid having the nucleotide sequence set forth in FIG. 10 (SEQ ID NO: 27). The recombinant proteins expressed by the nucleic acids described herein encompasses those proteins set forth in FIG. 10 (SEQ ID NO: 33). The recombinant proteins of virB11 described herein possess the ability to bind to antibodies present in IFA positive sera (and not IFA negative sera). The recombinant virB11 protein possesses the ability to react to IFA-positive sera.

In one embodiment, the present invention provides a recombinant polypeptide containing an amino acid sequence as set forth in SEQ ID NO: 32. In another embodiment, the present provides a recombinant polypeptide containing an amino acid sequence set forth in SEQ ID NO: 33.

It is understood that these recombinant polypeptides encompass variants. One type of variants includes modification of amino acids of recombinant polypeptides; such as, for example, substitution, deletion, or addition of amino acids. The present invention is intended to encompass the polypeptide variants of virB10 and virB11 that retain the antibody binding ability towards IFA sero-positive sera and do not react to IFA sero-negative sera from *Anaplasma* infected patients. One of ordinary skill in the art would recognize that conservative amino acid substitutions may include simply substituting glutamic acid with aspartic acid; substituting isoleucine with leucine; substituting glycine or valine, or any divergent amino acid, with alanine, substituting arginine or lysine with histidine, and substituting tyrosine and/or phenylalanine with tryptophan. In another embodiment, addition and deletion of single amino acid may be employed. It is also appreciated by one of ordinary skill in the art that a few amino acids can be included or deleted from each or both ends, or from the interior of the polypeptide without significantly altering the peptide's ability to bind antibody (i.e., maintain high sensitivity and specificity (>80%), when tested in an ELISA assay.

Recombinant Expression of virB10 and virB11 Polypeptides: Vectors and Hosts

Transcriptional and translational control sequences are DNA regulatory sequences, such as promoters, enhancers, terminators, and the like, that provide for the expression of a coding sequence in a host cell.

A DNA sequence is "operatively linked" or "operably linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted upstream (5') of and in reading frame with the gene. A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

In one embodiment, the present invention provides the expression of the DNA sequences disclosed herein. As is well known in the art, DNA sequences may be recombinantly expressed by operatively linking the sequences to an expression control sequence in an appropriate expression vector; and expressing that linked vector via transformation in an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence. A wide variety of host/expression vector combinations may be employed in expressing the DNA sequences of this invention. Useful expression vectors, for example, may consist of segments of chromosomal, non-chromosomal and Synthetic DNA sequences. Suitable vectors include pET, pENTR, and pCR®8/GW/TOPO® and the like. The promoter contains lac promoter, trp promoter and tac promoter.

In one embodiment, a host cell contains the vector comprising the polynucleotides of the present invention. Exemplary host cell includes *E. coli*. Various *E. coli* strains include, for example, NovaBlue strain, BL21 (DE3) or BL21 pLsS (DE3).

It will be understood that not all vectors, expression control sequences and hosts will function equally well to express the DNA sequences of this invention. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors, a person skilled in the art will be able to construct a variety of vector/expression control sequence/host combinations that will express the DNA sequences of this invention on fermentation or in large scale animal culture.

For recombinant expression of the various proteins used in this application, genes encoding the various proteins of interest can be conveniently inserted into a cloning vector and the vector containing the gene of interest is transfected or transformed into a suitable host cell for protein expression. Various publicly available vectors may be used. For example, vectors may include a plasmid, cosmid, viral particle, or phage. Examples of vectors included pET30, pENTR, pCR8/GW/TOPO and the like. Vector components generally include, but are not limited to, one or more of a signal sequence, an origin of replication, a marker gene, an enhancer element, a promoter, and a transcription termination sequence. Construction of suitable vectors containing one or more of these components as well as the gene of interest employs standard ligation techniques which are known to the skilled artisan.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Examples of suitable selectable markers for mammalian cells include those that enable the identification of cells competent to take up the antigen-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 (Stinchcomb et al., *Nature,* 282:39 (1979). The trp1 gene provides a selection marker for a mutant strain of yeast lacking the ability to grow in tryptophan, for example, ATCC No. 44076 or PEP4-1 (Jones, *Genetics,* 85:12 (1977)).

A number of promoters can be used in order to enhance the expression of the gene of interest. In one embodiment, a promoter can be employed which will direct expression of a polynucleotide of the present invention in *E. coli*. Other equivalent transcription promoters from various sources are known to those of skill in the art. Exemplary promoters include the β-lactamase and lactose promoter systems (Chang et al., Nature, 275:615 (1978)), alkaline phosphatase, a tryptophan (tip) promoter system (Goeddel, *Nucleic Acids Res.,* 8:4057 (1980)), and the like.

A promoter may be operably linked to the protein-encoding nucleic acid sequence to direct mRNA synthesis. Promoters recognized by a variety of potential host cells are well known. For example, promoters for use in bacterial systems also will contain a Shine-Dalgarno (S.D.) sequence operably linked to the DNA encoding the protein of interest.

Transcription of a DNA encoding the antigen by higher eukaryotes may be increased by inserting an enhancer sequence into the vector. Enhancers are cis-acting elements of DNA, usually about from 10 to 300 bp, that can act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the 15-kDa coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding *Anaplasma phagocytophilum* antigen.

The nucleic acid (e.g., genomic DNA) encoding recombinant *Anaplasma phagocytophilum* antigen of the present invention may be inserted into a replicable vector for cloning (amplification of the DNA) or for expression. For example, a type IV secretion system (TIVSS) protein, such as full-length virB9 (SEQ ID No. 25) may be inserted into a replicable vector for cloning and for expression of full-length virB9 protein or fragments thereof. The appropriate nucleic acid sequence may be inserted into the vector by a variety of procedures. In general, DNA is inserted into an appropriate restriction endonuclease site(s) using techniques known in the art.

Host cells are transfected or transformed with expression or cloning vectors described herein for antigen production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. These examples are illustrative rather than limiting.

Methods of eukaryotic cell transfection and prokaryotic cell transformation are known to the ordinarily skilled artisan, for example, $CaCl_2$, $Ca_2PO_4$, liposome-mediated and electroporation. Depending on the host cell used, transformation is performed using standard techniques appropriate to such cells. The calcium treatment employing calcium chloride, as described in Sambrook et al., or electroporation is generally used for prokaryotes. For mammalian cells without such cell walls, the calcium phosphate precipitation method of Graham and van der Eb, *Virology,* 52:456-457 (1978) can be employed. Transformations into yeast are typically carried out according to the method of Van Solingen et al., *J. Bact.,* 130:946 (1977). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, See Keown et al., Methods in Enzymology, 185:527-537 (1990). The particular selection of host/cloning vehicle combination may be made by those of skill in the art after due consideration of the principles set forth without departing from the scope of this invention (See, e.g., Sambrook et al., *Molecular Cloning, A Laboratory Manual* $2^{nd}$ edition, 1989, Cold Spring Harbor Press, NY).

The antigen may be recombinantly produced as a fusion polypeptide with a heterologous polypeptide. The heterologous polypeptide may serve as a signal sequence or other polypeptide having a specific cleavage site at the N-terminus of the mature protein or polypeptide. In general, the signal sequence may be a component of the vector, or it may be a part of the antigen-encoding DNA that is inserted into the vector. In mammalian cell expression, mammalian signal sequences may be used to direct secretion of the protein, such as signal sequences from secreted polypeptides of the same or related species, as well as viral secretory leaders. An overview of expression of recombinant proteins is found in *Methods of Enzymology v.* 185, Goeddel, D. V. ed. Academic Press (1990).

Recombinant gene expression may be measured in a sample directly, for example, by conventional Southern blotting, Northern blotting to quantitate the transcription of mRNA (Thomas, *Proc. Natl. Acad. Sci. USA,* 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Recombinant gene expression, alternatively, may be measured by immunological methods, such as immunohistochemical staining of cells or tissue sections and assay of cell culture or body fluids, to quantitate directly the expression of gene product. Antibodies useful for immunohistochemical staining and assay of sample fluids may be either monoclonal or polyclonal, and may be prepared in any mammal. Conveniently, the antibodies may be prepared against a native sequence polypeptide or against a synthetic peptide based on the DNA sequences provided herein or against exogenous sequence fused to *Anaplasma phagocytophilum* DNA and encoding a specific antibody epitope.

After expression, recombinant antigen may be recovered from culture medium or from host cell lysates. If membrane-bound, it can be released from the membrane using a suitable detergent solution (e.g. Triton-X 100) or by enzymatic cleavage. Cells employed in expression of *Anaplasm phagocytophilum* antigen can be disrupted by various physical or chemical means, such as freeze-thaw cycling, sonication, mechanical disruption, or cell lysing agents.

It may be desired to purify recombinant antigen from host cell proteins. The following procedures are exemplary of suitable purification procedures: by fractionation on an ion-exchange column; reverse phase HPLC; chromatography on silica or on a cation-exchange resin such as DEAE; chromatofocusing; SDS-PAGE; ammonium sulfate precipitation; metal chelating columns to bind epitope-tagged fauns of the protein of interest. Various methods of protein purification may be employed and such methods are known in the art and described for example in Deutscher, *Methods in Enzymology,* 182 (1990); Scopes, Protein Purification: Principles and Practice, Springer-Verlag, New York (1982). The purification step(s) selected will depend, for example, on the nature of the production process used and the particular antigen produced.

ELISA Assay

Detection of antibody binding in IFA sero-positive sera may be accomplished by techniques known in the art, e.g., ELISA (enzyme-linked immunosorbent assay), western blots, and the like. In one embodiment, antibody binding is assessed by detecting a label on the primary antibody. In another embodiment, the primary antibody is assessed by detecting binding of a secondary antibody or reagent to the primary antibody. In a further embodiment, the secondary antibody is labeled. Many means are known in the art for detecting binding in an immunoassay and are within the scope of the present invention. For example, to select specific epitopes of recombinant or synthetic polypeptide, one may assay antibody binding in an ELISA assay wherein the polypeptides or its fragments containing such epitope.

As appreciated by one skilled in the art, an enzyme-linked immunosorbent assay (ELISA) may be employed to detect antibody binding in IFA sero-positive sera. In an initial step of an ELISA, an antigen is immobilized onto a surface (for example by passive adsorption known as coating). For purposes of this application, exemplary antigens include *Anaplasma phagocytophilum* type IV secretion system proteins (e.g. virB10 and virB11), hemolysin, succinate dehydrogenase and p44-8 outer membrane protein and the like. Recombinant full-length protein as well as fragments thereof may be used. Immobilization of antigen may be performed on any inert support that is useful in immunological assays. Examples of commonly used supports include small sheets, Sephadex and assay plates manufactured from polyethylene, polypropylene or polystyrene. In a preferred embodiment the immobilized antigens are coated on a microtiter plate that allows analysis of several samples at one time. More preferably, the microtiter plate is a microtest 96-well ELISA plate, such as those sold under the name Nunc Maxisorb or Immulon.

Antigen immobilization is often conducted in the presence of a buffer at an optimum time and temperature optimized by one skilled in the art. Suitable buffers should enhance immobilization without affecting the antigen binding properties. Sodium carbonate buffer (e.g., 50 mM, pH 9.6) is a representative suitable buffer, but others such as Tris-HCl buffer (20 mM, pH 8.5), phosphate-buffered saline (PBS) (10 mM, pH 7.2-7.4) are also used. Optimal coating buffer pH will be dependent on the antigen(s) being immobilized. Optimal results may be obtained when a buffer with pH value 1-2 units higher than the isoelectric point (pI) value of the protein is used. Incubation time ranges from 2-8 hours to overnight. Incubation may be performed at temperatures ranging from 4-37° C. Preferably, immobilization takes place overnight at 4° C. The plates may be stacked and coated long in advance of the assay itself, and then the assay can be carried out simultaneously on several samples in a manual, semi-automatic, or automatic fashion, such as by using robotics.

Blocking agents are used to eliminate non-specific binding sites in order to prevent unwanted binding of non-specific antibody to the plate. Examples of appropriate blocking agents include detergents (for example, Tween-20, Tween-80, Triton-X 100, sodium dodecyl sulfate), gelatin, bovine serum albumin (BSA), egg albumin, casein, non-fat dried milk and the like. Preferably, the blocking agent is BSA. Concentrations of blocking agent may easily be optimized (e.g. BSA at 1-5%). The blocking treatment typically takes place under conditions of ambient temperatures for about 1-4 hours, preferably 1.5 to 3 hours.

After coating and blocking, sera from the control (IFA sero-negative) or IFA sero-positive patients are added to the immobilized antigens in the plate. Biological sample (i.e., sera) may be diluted in buffer. Phosphate Buffered Saline (PBS) containing 0.5% BSA, 0.05% TWEEN 20® detergent may be used. TWEEN 20® acts as a detergent to reduce non-specific binding.

The conditions for incubation of the biological sample and immobilized antigen are selected to maximize sensitivity of the assay and to minimize dissociation. Preferably, the incubation is accomplished at a constant temperature, ranging from about 0° C. to about 40° C., preferably from about 22 to 25° C. to obtain a less variable, lower coefficient of variant (CV) than at, for example, room temperature. The time for incubation depends primarily on the temperature, being generally no greater than about 10 hours to avoid an insensitive assay. Preferably, the incubation time is from about 0.5 to 3 hours, and more preferably 1.5-3 hours at room temperature to maximize binding to immobilized capture antigen.

Following incubation of the biological sample and immobilized antigen, unbound biological sample is separated from the immobilized antigen by washing. The solution used for washing is generally a buffer ("washing buffer") with a pH determined using the considerations and buffers described above for the incubation step, with a preferable pH range of about 6-9. Preferably, pH is 7. The washing may be done three or more times. The temperature of washing is generally from refrigerator to moderate temperatures, with a constant temperature maintained during the assay period, typically from about 0-40° C., more preferably about 4-30° C. For example, the wash buffer can be placed in ice at 4° C. in a reservoir before the washing, and a plate washer can be utilized for this step.

Next, the immobilized capture antigen and biological sample are contacted with a detectable antibody at a time and temperature optimized by one skilled in the art. Detectable antibody may include a monoclonal antibody or a polyclonal antibody. These antibodies may be directly or indirectly conjugated to a label. Suitable labels include moieties that may be detected directly, such as fluorochrome, radioactive labels, and enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, horseradish peroxidase (HRP), alkaline phosphatase, and the like. Preferably, the detection antibody is a goat anti-human IgG polyclonal antibody that binds to human IgG and is directly conjugated to HRP. Incubation time ranges from 30 minutes to overnight, preferably about 60 minutes. Incubation temperature ranges from about 20-40° C., preferably about 22-25° C., with the temperature and time for contacting the two being dependent on the detection means employed.

The conjugation of such labels to the antibody, including the enzymes, is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166.

Because IgG may occasionally interfere in IgM detection assays, IgG in patient sera may be removed prior to IgM ELISA. Ideally, an anti-human IgG antibody is used to neutralize the IgG in human sera. Commercial reagents such as GullSORB™ (Meridian Bioscience, Inc., Cincinnati, Ohio) may be used. The method for IgG removal can be conveniently optimized by one of ordinary skill in the art. For example, human sera can be incubated with anti-human IgG antibody prior to the IgM ELISA assay.

Diagnostic Kits Employing Recombinant virB10 and virB11 Polypeptides

The present invention provides a kit for the diagnosis of *anaplasma* infection. In one embodiment, the kit is an ELISA kit containing recombinant polypeptides described herein, detection reagents including primary or secondary antibodies, and other necessary reagents including enzyme substrates and color reagents. Additional components that may be present within such kits include an instruction detailing the detection procedure for *Anaplasma phagocytophilum*, using the recombinant polypeptides of the present invention. The diagnostic kit of the present invention further comprises a positive and negative serum control. The diagnostic kit of the present invention can also be used in diagnosing other infectious diseases involving *Anaplasma phagocytophilum* such as Human Granulocytic Anaplasmosis (HGA).

The following Examples are offered by way of illustration and not by way of limitation.

EXPERIMENTAL STUDIES

Example 1

Type IV Secretion System in *Anaplasma phagocytophilum*

FIG. 1 is a schematic depiction of the Type IV Secretion System (TIVSS) in plant pathogen *Agrobacterium tumefaciens* (modified from Kyoto Encyclopedia of Genes and Genomes (KEGG) (http://www.genome.ad.jp/dbgetbin/get_pathway?org_name=aph&mapno=03080). TIVSS is believed to form a conduit for transportation of macromolecules such as proteins and DNA across the cell membrane. TIVSS in *Agrobacterium tumefaciens* represents a prototype, albeit the protein components within the TIVSS may vary among the different pathogens. For example, while *Agrobacterium* spp. have twelve (12) proteins (See, FIG. 1), *Anaplasma phagocytophilum* (a phylogenetically distant species) contains only eight (8) proteins. Notably, virB1, virB2, virB5 and virB7 are absent in *Anaplasma phagocytophilum*. The exact structural organization of TIVSS in *Anaplasma phagocytophilum* is presently unclear.

TIVSS is essential for establishing infection in *Anaplasma phagocytophilum*. There is no information about the immunogenicity of the various TIVSS proteins during the *anaplasma* infection. So far in *Anaplasma phagocytophilum*, a non-TIVSS protein (p44; a surface protein) is known to induce an antibody response in a human host (Ijdo, J. W. et al., Cloning of the gene encoding the 44-kilodalton antigen of the agent of human granulocytic ehrlichiosis and characterization of the humoral response. *Infection and Immunity,* 66(7): 3264-3269, 1998).

The present inventors surprisingly discovered that two (2) of the TIVSS protein components are good candidate biomarkers for the diagnosis of *Anaplasma phagocytophilum* infection. Evidence is presented herein to demonstrate that recombinantly expressed virB10 and virB11, when immobilized in an ELISA assay, are good detection markers for an IgG/IgM antibody response to *Anaplasma phagocytophilum* infection.

Figure 2:
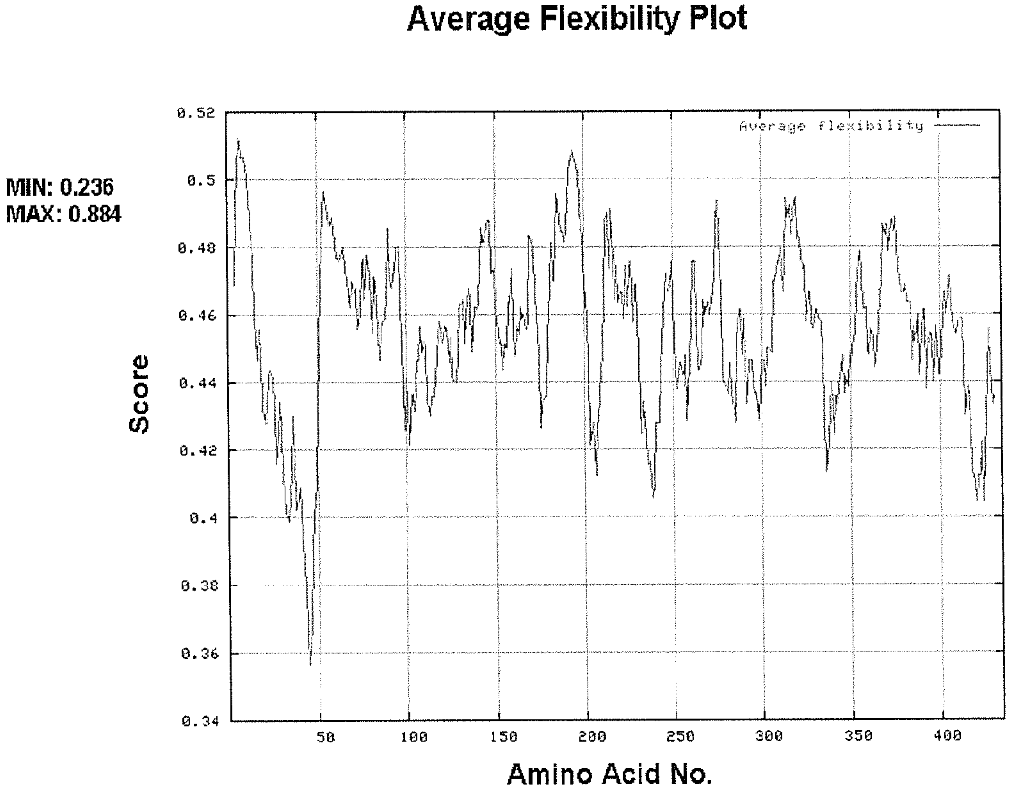
FIG. 2 depicts the Average Flexibility Plot for one of the eight (8) TIVSS proteins (i.e., virB10).
Figure 3:
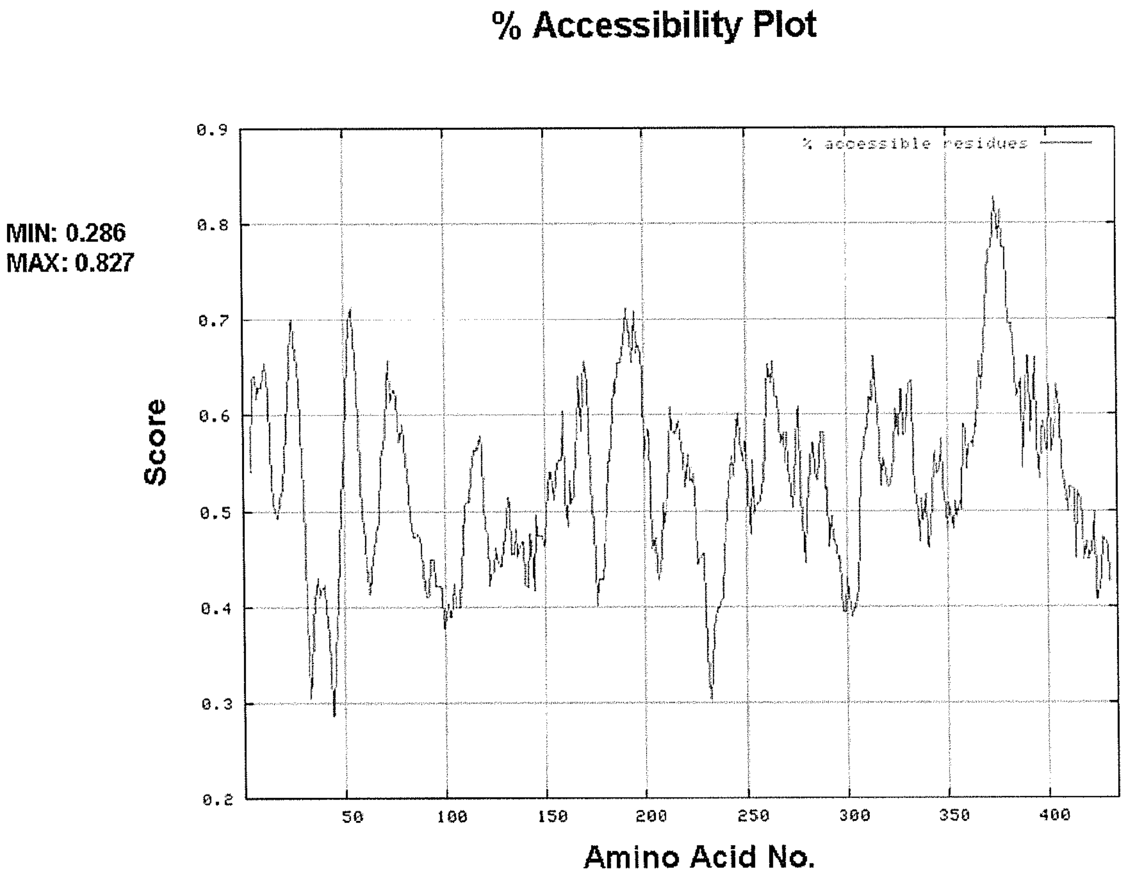
FIG. 3 depicts the % Accessibility Plot for one of the eight (8) TIVSS proteins (i.e., virB10).
Figure 4:
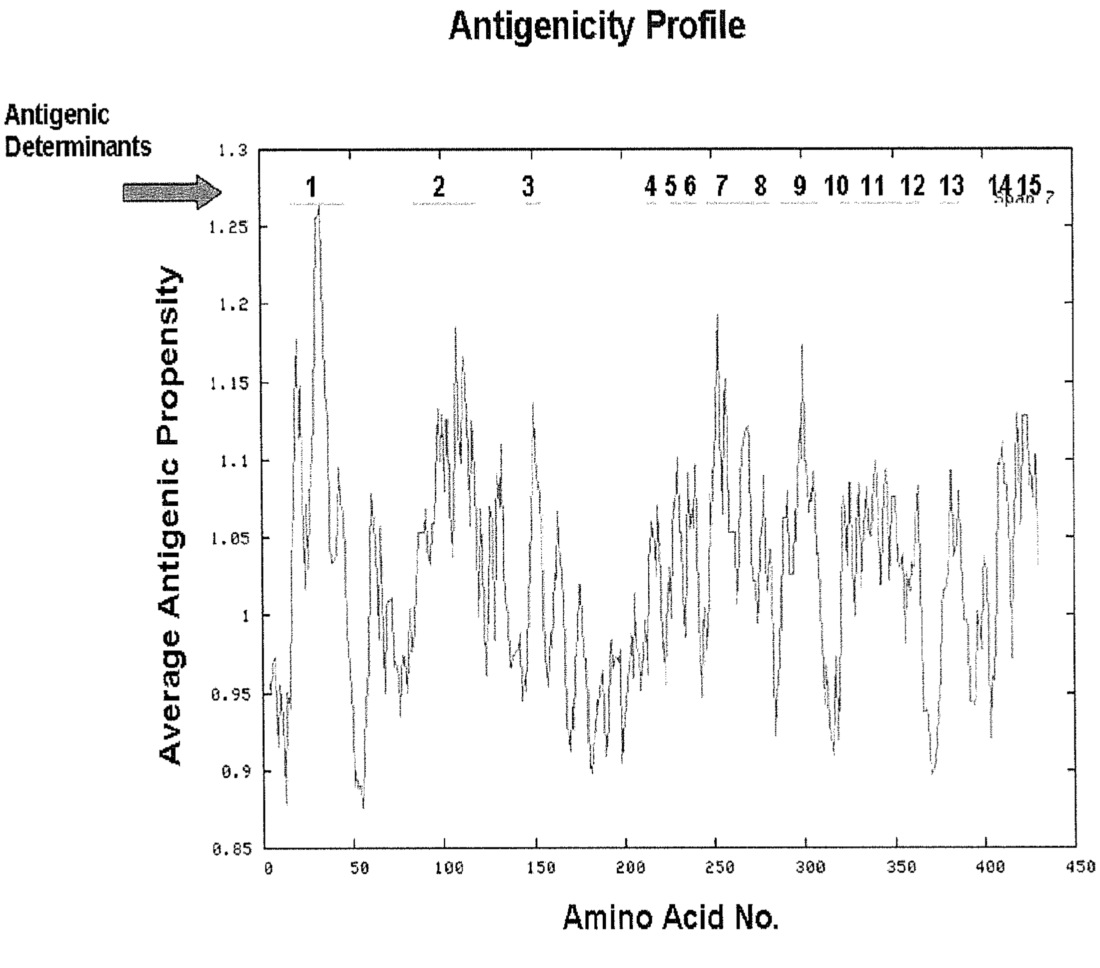
FIG. 4 depicts the Antigenicity Profile for one of the eight (8) TIVSS proteins (i.e., virB10).

As an initial step, we used an in silico analysis to examine TIVSS. We analyzed various structural features of the TIVSS protein components in *Anaplasma phagocytophilum* for their possible antigenic potential. Specifically, we examined: (i) % accessible residues, and (ii) average flexibility. We further analyzed the predicted antigenicity for each of the eight (8) TIVSS proteins. For illustration purposes, results of in silico analysis for virB10 are shown. FIG. 2 shows the average flexibility plot for virB10, FIG. 3 shows the. % accessibility plot for virB10. FIG. 4 shows the antigenicity profile for virB10. In sum, in silico analysis reveals that there are multiple potential antigenic determinants that may be present in the eight (8) TIVSS proteins in *Anaplasma phagocytophilum* (See, FIG. 4).

Tables 1 and 2 summarizes the results of the in silico analysis. They show that all of the eight (8) TIVSS protein components in *Anaplasma phagocytophilum* (Table 1) have regions that could be potential epitopes for antibody recognition and binding. Similarly, three (3) non-TIVSS protein components in *Anaplasma phagocytophilum* also reveal many potential antigenic epitopes. Although in silico analysis provides a theoretical predication that all of the TIVSS protein components could potentially be antigenic candidates, it cannot provide absolute certainty as to which, if any, TIVSS component(s) actually serve as a good biomarker for *anaplasma* detection.

Example 2

Cloning and Expression of Various TIVSS Protein Components: (virB3, virB4, virB6, virB8, virB9, virB10, virB11 and virD4)

PCR Amplification and Ligation into Plasmid Vector

In order to determine if any of the TIVSS proteins is/are epitopes for antibody recognition, we cloned and recombinantly expressed the various TIVSS protein components in *Anaplasma phagocytophilum*.

In our cloning strategy, we designed and prepared synthetic oligonucleotides (~30 bp in length) and used them to amplify eight (8) of the genes that encod TIVSS. This included virB3, virB4, virB6, virB8, virB9, virB10, virB11 and virD4. We also cloned two (2) non-TIVSS proteins (i.e., succinate dehydrogenase iron-sulfur subunit and p44 outer membrane protein) and used for comparison purposes. Table 3 shows the nucleotide sequence of the various oligonucleotides (i.e., SEQ ID Nos. 1-20) used in the PCR amplification reaction.

Genomic DNA of *Anaplasma phagocytophilum* (a generous gift from Dr. S. Dumler at Johns Hopkins University) was used as the template for each of the PCR reactions. Synthetic oligonucleotides corresponding to each of the TIVSS genes were used for the PCR amplification reactions. Using the synthetic oligonucleotides (sequence listed in Table 3) and genomic DNA from *Anaplasma phagocytophilum*, we successfully amplified six (6) of the TIVSS genes; namely, virB3, virB6, virB9, virB10, virB11, virD4; as well as two (2) non-TIVSS genes (i.e., succinate dehydrogenase iron-sulfur and p44 proteins) (See, FIGS. 5 and 6). However, the synthetic oligonucleotides used for virB4 and virB8 did not lead to any amplification product (See, FIGS. 5 and 6).

Figure 5:
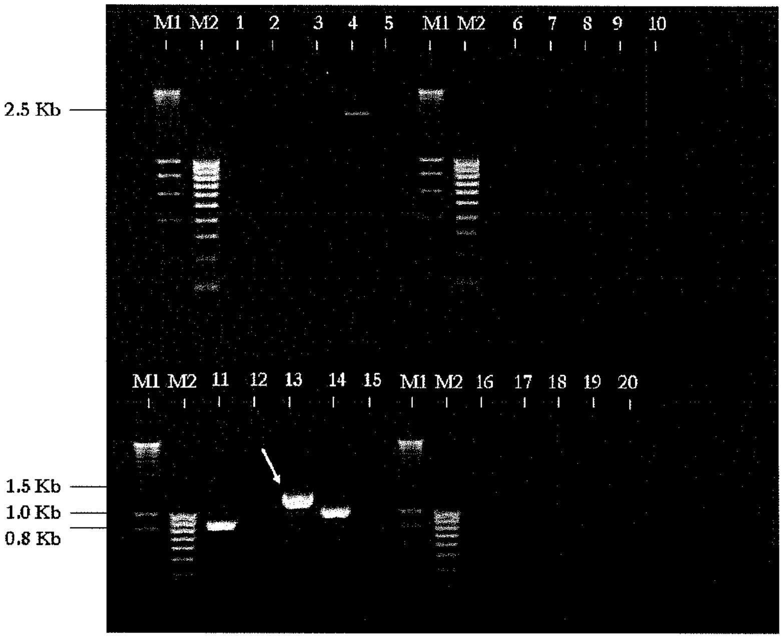
FIG. 5 depicts the EK/LIC PCR Amplification of *Anaplasma* Genes Encoding TIVSS proteins of *Anaplasma phagocytophilum.*
Figure 6:
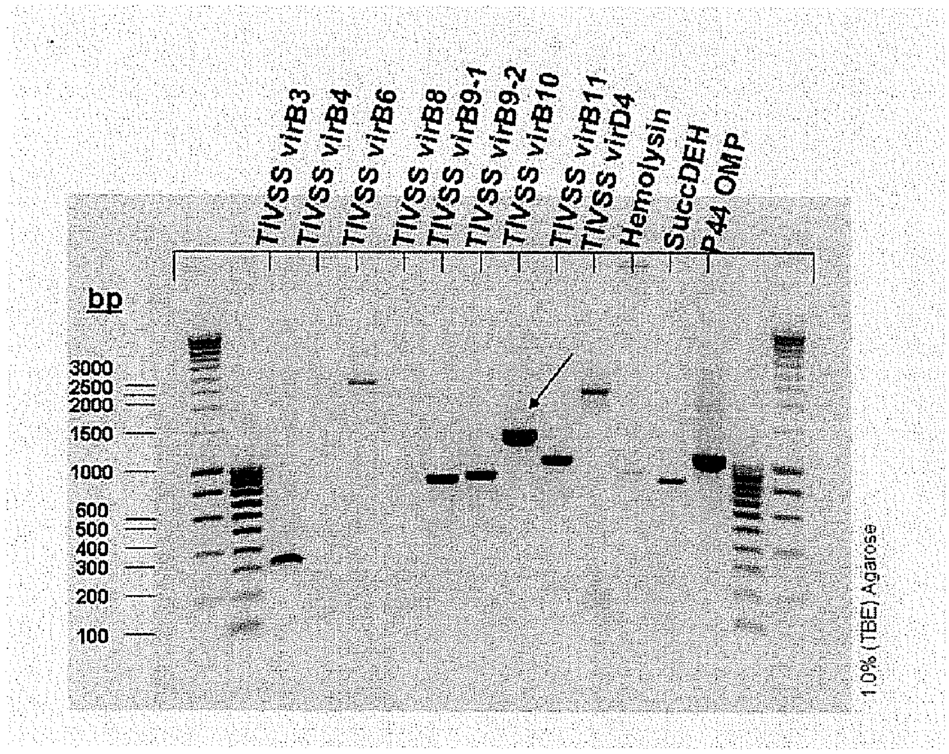
FIG. 6 depicts the Post-PCR Clean-Up of *Anaplasma* Clones for Recombinant Expression.

FIG. 5 shows an agarose gel of the amplified genes prior to processing of the PCR reactions in preparation for ligation into pET30 vector. The virB10 amplicon having an expected size (~1.0 kb) is shown by the arrow in this figure. In preparation for ligation with the vector, the PCR amplification reactions were treated to remove any remaining nucleotides, primers, and reaction components. FIG. 6 shows a coomassie-stained gel of the amplified genes following clean-up of the PCR reactions. The arrow in this figure shows the virB10 amplicon of expected size (~1.0 Kb). The resulting PCR products were then treated with T4 DNA polymerase and ligated into pET30 using standard protocols (See, FIG. 7). Ligation of insert DNA (including virB3, virB6, virB9, virB10, virB11, virD4, succinate dehydrogenase iron-sulfur and p44 proteins) was performed as described below.

T4 Polymerase Treatment of PCR Products and Ligation into pET30 Vector

Figure 7:
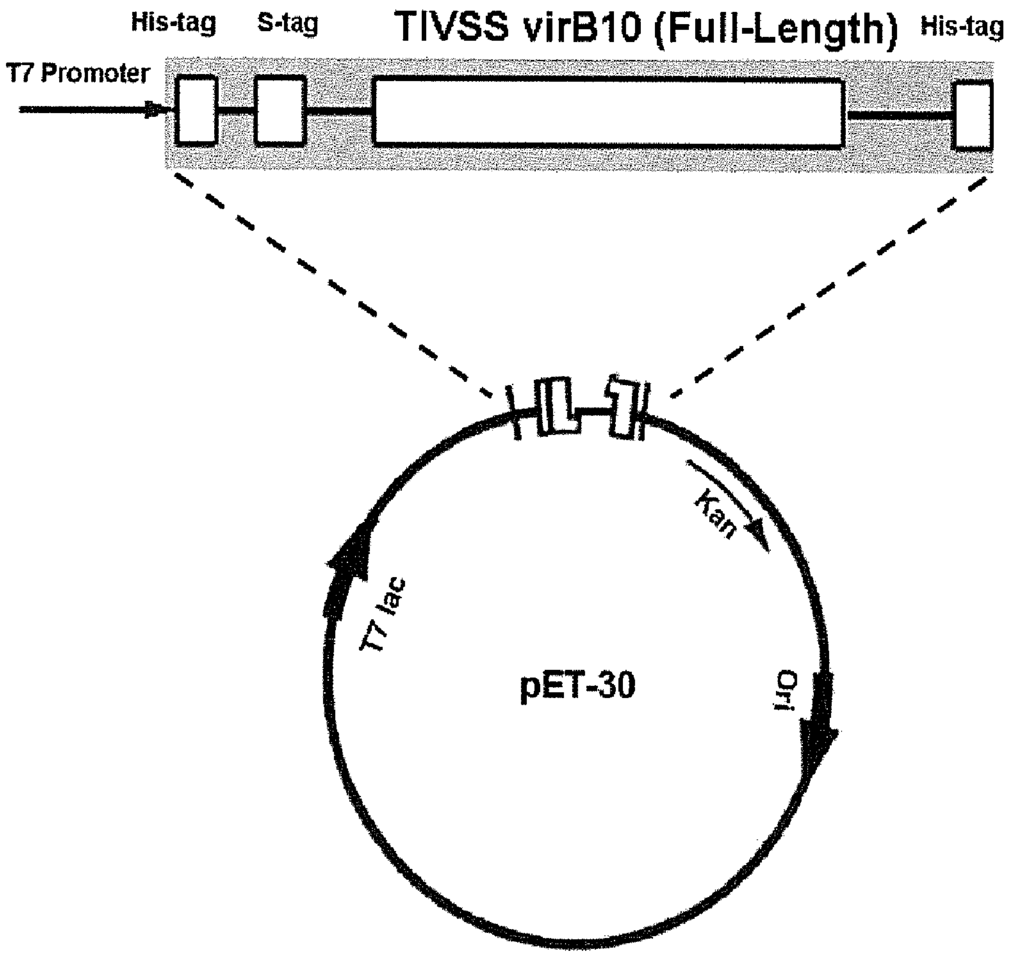
FIG. 7 depicts the pET-30 Vector Containing TIVSS Genes (e.g., virB10).

In order to ligate the cloned insert DNA with the plasmid vector, it is necessary to create compatible ends between the amplicon and the chosen vector (e.g., pET30 Ek/LIC). We generated overhangs compatible with the Ek/LIC cloning vector on the insert DNA by T4 DNA polymerase treatment of the PCR amplicon. We ligated the treated amplicon into the expression vector to form pET30/insert DNA. FIG. 7 depicts the pET30 vector containing the inserted gene (e.g., full-length virB3, virB6, virB9, virB10, virB11, virD4, succinate dehydrogenase iron-sulfur and p44). The nucleotide sequences of virB3, virB6, virB9, virB10, virB11, virD4, succinate dehydrogenase iron-sulfur and p44 are publicly available and their accession numbers are listed in Table 3.

Transformation of Recombinant Clones into NovaBlue *E. coli*

In these series of experiments, we transformed the ligated DNAs (annealing reaction) into host bacterial cells (NovaBlue *E. coli*). The ligated DNAs included virB3, virB6, virB9, virB10, virB11, virD4 amplicons as well as succinate dehydrogenase iron-sulfur and p44 amplicons. We chose NovaBlue *E. coli* because this bacterial strain is optimized for producing a stable cell line containing a recombinant insert (see, NovaBlue Ek/LIC manual). Transformation into NovaBlue competent *E. coli* (Novagen) was performed using standard protocols. First, appropriate numbers of 20 μl aliquots of competent cells were prepared from −80° C., and allowed to thaw on ice for several minutes, followed by the addition of 1 μl of the annealing reaction and gentle stirring. The mixture was further incubated on ice for an additional 5 minutes, followed by heating the tubes for 30 seconds in a 42° C. water bath. The tubes were immediately placed on ice for 2 minutes. SOC (Super Optimal broth with Catabolite repression medium, containing 2% w/v bacto-tryptone, 0.5% w/v bacto-yeast extract, 10 mM NaCl, 2.5 mM KCl, 10 mM $MgCl_2$, 20 mM glucose) (at room temperature) was added into the tubes, and the reactions were further incubated for 1 hour at 37° C. with shaking (250 rpm). Cells were plated onto LB agar plates (containing kanamycin) and incubated at 37° C. overnight.

Colony PCR of NovaBlue Transformants

To confirm the successful transformation of insert DNA (pET30/insert DNA) in *E. coli* cells, we selected several colonies of each transformant grown on LB plates (with kanamycin), and performed colony PCR using the same set of Ek/LIC primers as in the amplification of the genes from the *Anaplasma* genomic DNA. An aliquot of each PCR reaction was analyzed using agarose gel electrophoresis.

Figure 11:
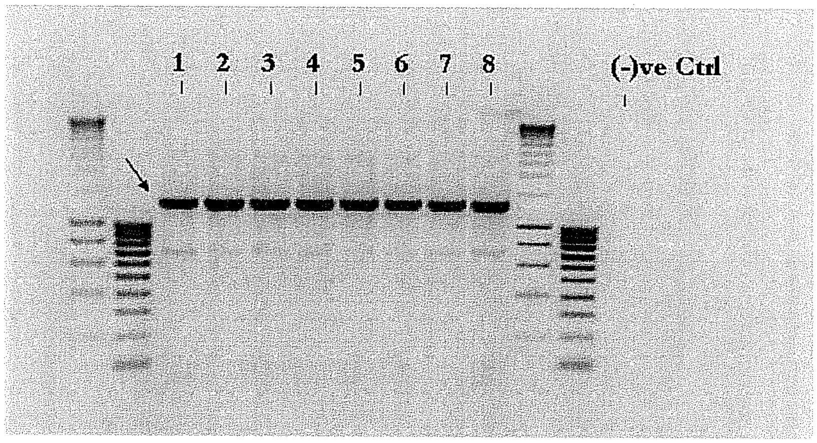
FIG. 11 depicts the Colony PCR of Transformants in NovaBlue *E. coli.*
Figure 12:
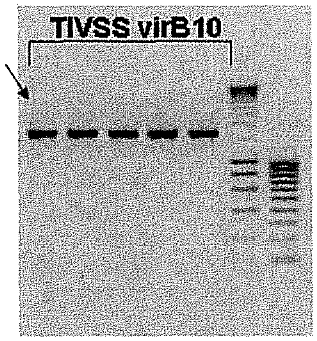
FIG. 12 depicts the Colony PCR of Transformants in BL21 (DE3) *E. coli.*

As an example, FIG. 11 shows agarose gel electrophoresis analysis of eight of virB10 transformants in NovaBlue *E. coli*. Amplicons of expected size (1,100 bp) (arrow) were observed following analysis of the PCR reactions. NovaBlue *E. coli* colonies containing the pET30/insert DNA were further cultured in LB-kanamycin broth (for the isolation of plasmids).

Plasmid Mini-Preps

In order to confirm the presence and sequence accuracy of the cloned insert DNA in the pET30 vector, we performed sequence analysis on the recombinant plasmids. The sequence analysis also provides information that the insert was in-frame of the upstream His-tag sequence. First, we isolated plasmid DNA from the transformed *E. coli*. Wizard Plus SV Minipreps DNA Purification system (Promega) was used according to the manufacturer's recommended protocol. The concentration (1 $OD_{260/280}$=0.5 mg/ml) and the relative purity ($OD_{260/280}$) of the isolated plasmid DNA preparations were determined by spectrophotometric analysis.

Sequencing Analysis of Insert DNA

We next performed sequence analysis on the isolated plasmid DNA using the Applied BioSystems 3130 Genetic Analyzer DNA Sequencing instrument. All of the insert DNA were confirmed to be accurate by BLAST analysis and in-frame. As examples, the sequence analysis of the isolated plasmid DNA for virB9 virB10 and virB11) is summarized in FIGS. 8, 9 and 10. FIG. 8 depicts polynucleotide sequence encoding virB9, together with its deduced amino acid sequence. FIG. 9 depicts polynucleotide sequence encoding virB10, together with its deduced amino acid sequence. FIG. 10 depicts polynucleotide sequence encoding virB11, together with its deduced amino acid sequence. BLAST (Basic Local Alignment Search Tool, http://blast.ncbi.nlm.nih.gov/Blast.cgi) analysis of the sequences confirmed a match between each of the nucleotide sequences and the published sequences of the respective *Anaplasma phagocytophilium* genes.

Transformation of BL21 (DE3) *E. coli* with Recombinant Plasmids

After confirmation of the obtained recombinant plasmids, we proceeded to transform them into BL21 (DE3) competent *E. coli* (Novagen). Transformation was carried out by removing the appropriate number of 20 μl aliquots of competent cells from −80° C., allowing the tubes to thaw on ice for several minutes, followed by the addition of 1 μl of the plasmid preparation to the cells with gentle stirring. The mixture was incubated on ice for 5 minutes, followed by heating of the tubes for exactly 30 seconds in a 42° C. water bath. The tubes were immediately placed on ice for 2 min. SOC (room temperature) was added, and the reactions were further incubated at 37° C. for 1 hour at 250 rpm. Cells were then plated onto LB agar plated (containing kanamycin) and incubated at 37° C. overnight.

Colony PCR of BL21 (DE3) Transformants

To confirm the successful transformation of recombinant pET30/insert DNA in BL21 (DE3) *E. coli* cells, we selected several colonies of each transformant grown on LB plates (with kanamycin), and performed colony PCR using forward and reverse vector-specific primers. An aliquot of each PCR reaction was analyzed using agarose gel electrophoresis. FIG.

12 shows agarose gel electrophoresis analysis of five (5) of virB10 transformants in BL21 (DE3) *E. coli*. Amplicons of expected size (~1,100 bp) (arrow) were observed following analysis of the PCR reactions. Several BL21 (DE3) *E. coli* colonies containing the pET30/insert DNA were then processed for recombinant expression.

In addition to virB10, we also confirmed the successful transformation of recombinant pET30/insert DNA for virB3, virB6, virB9, virB11, virD4, succinate dehydrogenase iron-sulfur and p44.

Expression of Various Recombinant TIVSS Proteins in *E. coli*: (virB3, virB6, virB9, virB10, virB11 and virD4) and Non-TIVSS Proteins (Succinate Dehydrogenase Iron-Sulfur Subunit, and p44 Protein)

Figure 13:
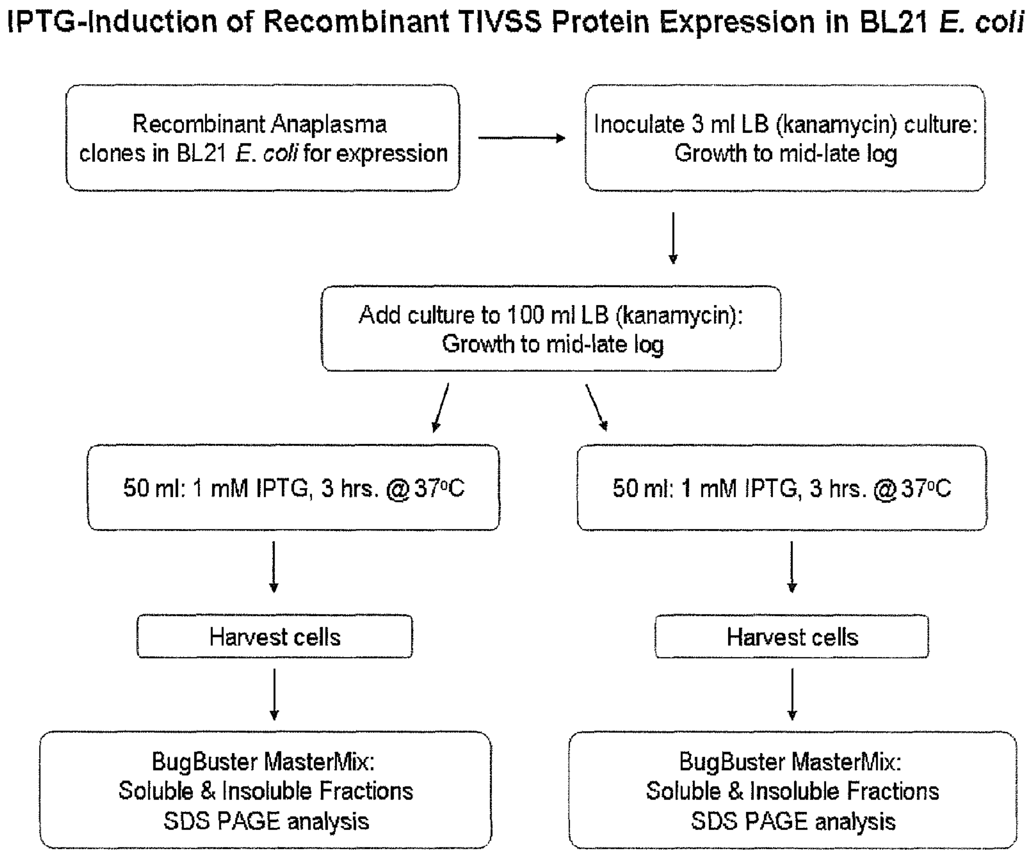
FIG. 13 depicts the protocol for IPTG-Induced Recombinant TIVSS Protein Expression in BL21 *E. coli.*

FIG. 13 depicts a flow chart depicting the steps for IPTG induction of recombinant TIVSS proteins in BL21 *E. coli*. For expression of various recombinant TIVSS (rTIVSS) proteins (for example, virB3, virB6, virB9, virB10, virB11, and virD4) and non-TIVSS proteins (for example, succinate dehydrogenase iron-sulfur submit and p44), BL21 (DE3) *E. coli* were transformed with the pET30-rTIVSS plasmid DNA containing the respective genes.

The expression was induced with IPTG as follows: 3 ml of LB broth cultures with kanamycin (30 μg/ml final concentration) were inoculated with BL21 transformed with pET30-rTIVSS plasmid. Cultures were grown to mid-log phase ($OD_{600}$=0.5) at 37° C. with shaking at 250 rpm. When the cultures reached mid-log, the entire 3 ml was added to 100 ml LB broth with kanamycin (30 μg/ml final concentration) and allowed to grow to mid-late log phase ($OD_{600}$=0.5-1). When the cultures reached mid-late log stage, they were split into two separate 50 ml batches in 250 ml flasks. To one flask, 500 μl of IPTG was added (final concentration of 1 mM). No IPTG was added to the other flask which served as a control for assessing induction. Growth of the IPTG and control cultures was allowed to proceed for 3-3.5 hours at 37° C. with shaking (250 rpm). Cell pellets were then harvested by centrifugation at 3,000 rpm for 15 minutes at 4° C., and subsequently processed with BugBuster Master Mix (Novagen) as described below.

Recombinant Expression of virB3, virB6, and Succinate Dehydrogenase Iron-Sulfur Subunit Fail After IPTG induction and BugBuster Master Mix treatment, equal concentrations (~3 μg) of a soluble cytoplasmic and insoluble (inclusion body) fraction from IPTG-treated cells and control cells were analyzed on SDS-PAGE. SDS-gels were stained using Coomassie-blue. Induction of recombinant protein expression was considered to be successful when there was a marked increase (observed on SDS-PAGE protein gels) in the target protein expression in the IPTG-treated sample, as compared to that of the control cells (i.e., no IPTG).

Figure 14:
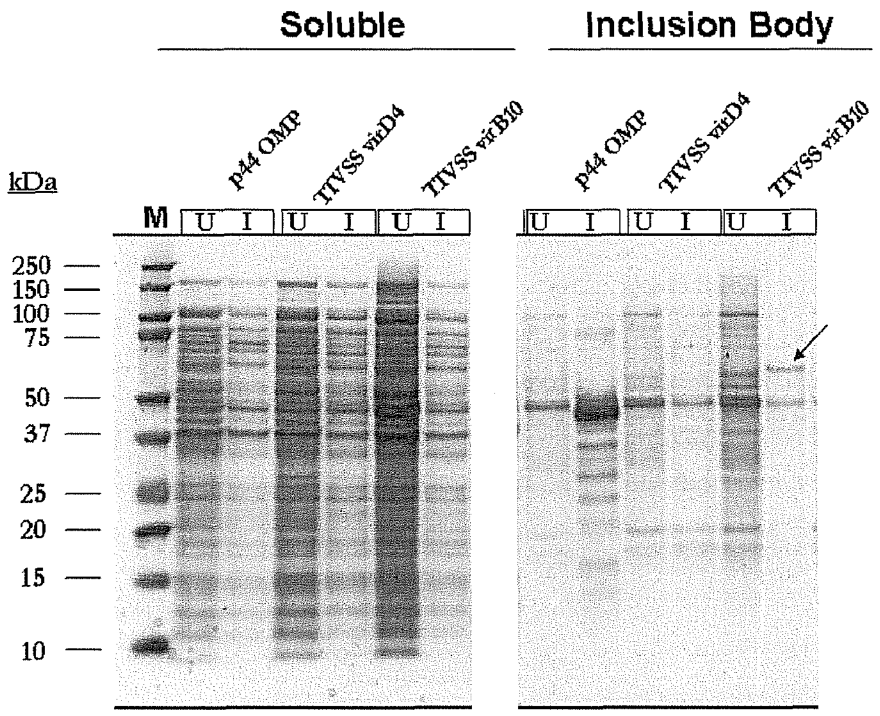
FIG. 14 depicts the IPTG Induction of TIVSS Protein (Soluble v. Insoluble Fractions).
Figure 15:
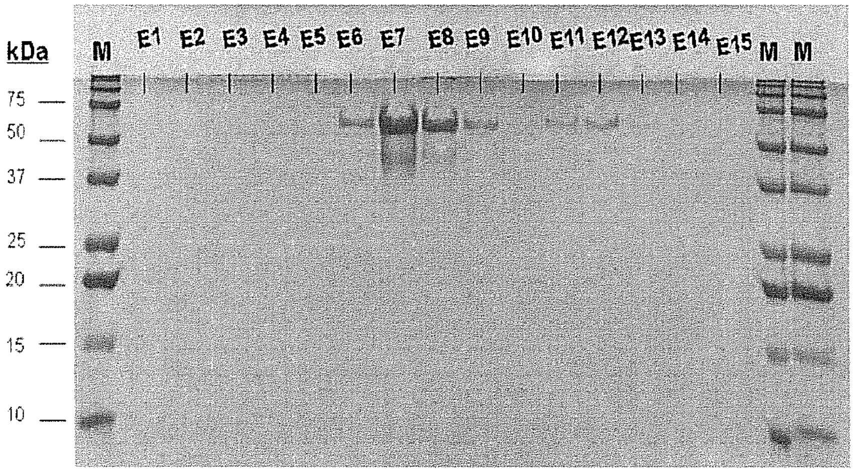
FIG. 15 depicts the Ni-NTA Purification of 6×His-Tagged Recombinant TIVSS Proteins.

FIG. 14 shows that IPTG induction of recombinant TIVSS proteins (soluble and inclusion body) before and after IPTG induction. Note that virB10 shows marked induction relative to the control (uninduced), and the induced virB10 is predominantly sequestered within the inclusion body fraction (see arrow).

Table 4 summarizes the results of recombinant expression of TIVSS. Using our expression protocol, we found that virB3 and virB6 fail to express any recombinant protein. We also noted a lack of expression in succinate dehydrogenase iron-sulfur subunit (Table 4).

Altogether, our results show that virB4 and virB8 genes could not be amplified under these experimental conditions. Unexpectedly, virB3 and virB6 failed to recombinantly express their corresponding proteins. We were successful in recombinantly express only four (4) of the eight (8) TIVSS protein components (namely, virB9, virB10, virB11, and virD4) in *Anaplasma phagocytophilum*. In addition, we were only able to recombinantly express p44 outer membrane protein, but not succinate dehydrogenase iron-sulfur subunit (See, Table 3 & Table 4).

Isolation and Purification of Recombinant virB9, virB10, virB11, virD4 and P44 Proteins Isolation of the expressed recombinant virB9, virB10, virB11 and virD4 proteins was performed using BugBuster Master Mix (Novagen) according to the manufacturer's protocol. After IPTG induction, bacterial cells were harvested from liquid cultures by centrifugation at 3,000 rpm for 15 minutes. Recombinant TIVSS proteins were isolated both from supernatant and cell pellets. Cell pellets were re-suspended in 5 ml of BugBuster Master Mix (Novagen) by gentle vortexing. The resulting cell suspensions were incubated on a rotating mixer for 20 minutes at room temperature. The mixtures were centrifuged at 4° C. for 20 minutes at 16,000×g to remove the insoluble cellular debris. The supernatant was transferred to a fresh tube for SDS PAGE analysis.

The pellet was then processed to isolate the insoluble cytoplasmic fraction, which consists of cell debris and aggregated protein (inclusion bodies). Inclusion body purification was carried out by re-suspending the pellet in the same volume (5 ml) of 1X BugBuster Master Mix used to re-suspend the original cell pellet. The mixtures were vortexed, followed by the addition of 20 ml of 1:10 diluted BugBuster Master Mix. The suspensions were vortexed, and then centrifuged at 5,000×g for 15 minutes at 4° C. to collect the inclusion body fraction. The pellets were re-suspended in 15 ml of 1:10 diluted BugBuster Master Mix, vortexed, and centrifuged at 5,000×g for 15 min. at 4° C. This step was repeated, with the centrifugation carried out for 15 minutes at 16,000×g. The supernatant was discarded, and the pellets re-suspended in 500 μl of PBS. An aliquot of the purified inclusion body fraction was analyzed on an SDS PAGE gel. Both the soluble and insoluble cytoplasmic fractions of TIVSS proteins were combined for ELISA tests.

Example 3

IgG/IgM ELISA for Recombinantly Expressed TIVSS Protein Components

We adopted IgG and IgM ELISA assays and evaluated the binding activity of the recombinant proteins towards IgG and IgM. The ELISA procedure involves: (i) coating 96-well micro-titer plates with the recombinant protein at varying concentrations at 4° C. overnight; (ii) adding 5% non-fat milk to block non-specific binding; (iii) adding patients' sera to allow formation of antibody-antigen complex; (iv) detecting the antibody-antigen complex. IFA sero-positive sera served as positive controls, and IFA sero-negative sera served as negative controls. Detection of antibody-antigen complex was performed with the use of horseradish peroxidase.

a) Patient Study: virB9

We conducted both IgM and IgG ELISA tests for binding activity towards the recombinantly expressed TIVSS proteins.

Figure 16:
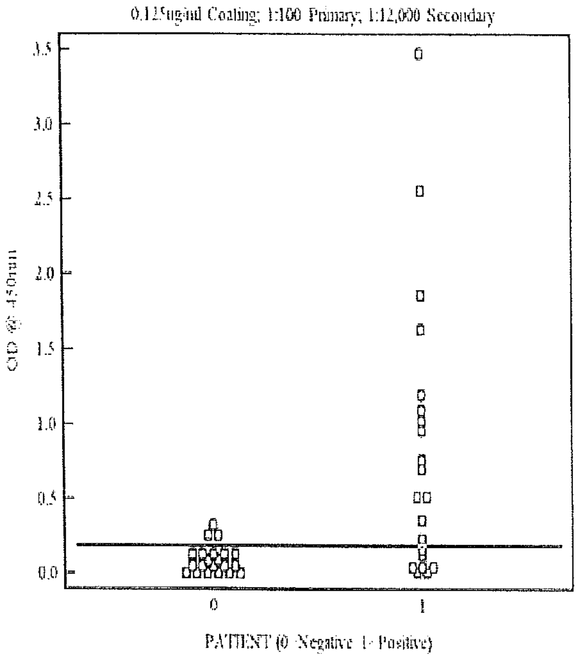
FIG. 16 depicts the IgM and IgG ELISA data for Recombinant virB9 of *Anaplasma phagocytophilum.*

In the first series of studies, we examined recombinant virB9 in an IgM ELISA. Recombinant virB9 was prepared using the cloning-expression method detailed above. When tested, we observed a dose-dependent increase in the binding activity (as measured by $OD_{45}$nm) towards IgM sero-positive sera (FIG. 16). The sensitivity of the IgM ELISA for recombinant virB9 was found to be 66.7%. The specificity of the IgM ELISA was 85.7% (See, FIG. 16). This level of sensitivity may be viewed by one of ordinary skill in the industry to be unsatisfactory. A threshold level of ≧70% is normally considered by industrial standard to be meaningful and acceptable for accurate interpretation of ELISA sensitivity.

FIG. 16 summarizes the binding of IgG sero-positive serum to recombinant virB9. We observed that there was no meaningful binding activity of virB9 towards IgG sero-positive sera, and significant cross-reactivity towards the IgG sero-negative sera. The cross-reactivity is indicative of false-positive result (i.e., low specificity). Note that virB9 IgG ELISA had failed checkerboard analysis (i.e., both sensitivity and specificity ≦60%). In sum, recombinant virB9 protein failed both sensitivity and specificity when tested for its binding ability towards IgG sero-positive and sero-negative serum.

Figure 16A:
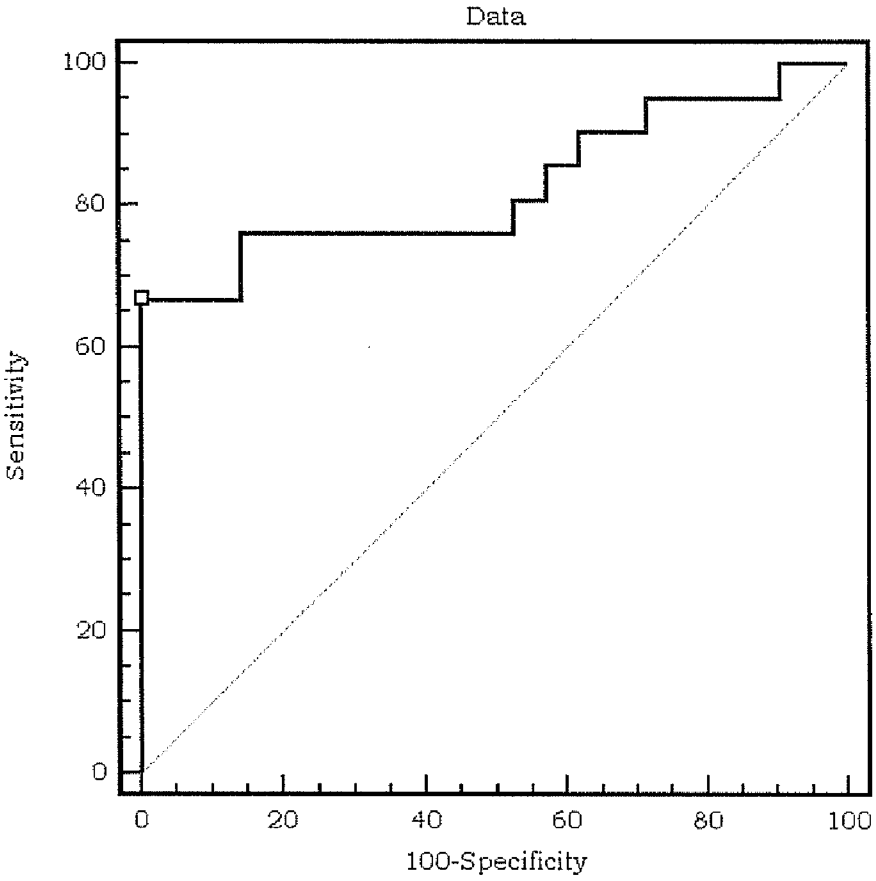
FIG. 16*a* depicts the ROC analysis for recombinant virB9 IgM ELISA.

Because virB9 only provides adequate IgM ELISA, we analyzed ROC (area under the curve) using the raw IgM ELISA data with the MedCalc statistical software. FIG. 16*a* summarizes the performance analysis of the ROC curve. AUC for recombinant virB9 is 0.828 (95% confidence interval; range: 0.680-0.926) (FIG. 16*a*).

b) Patient Study: virB10

Figure 17:
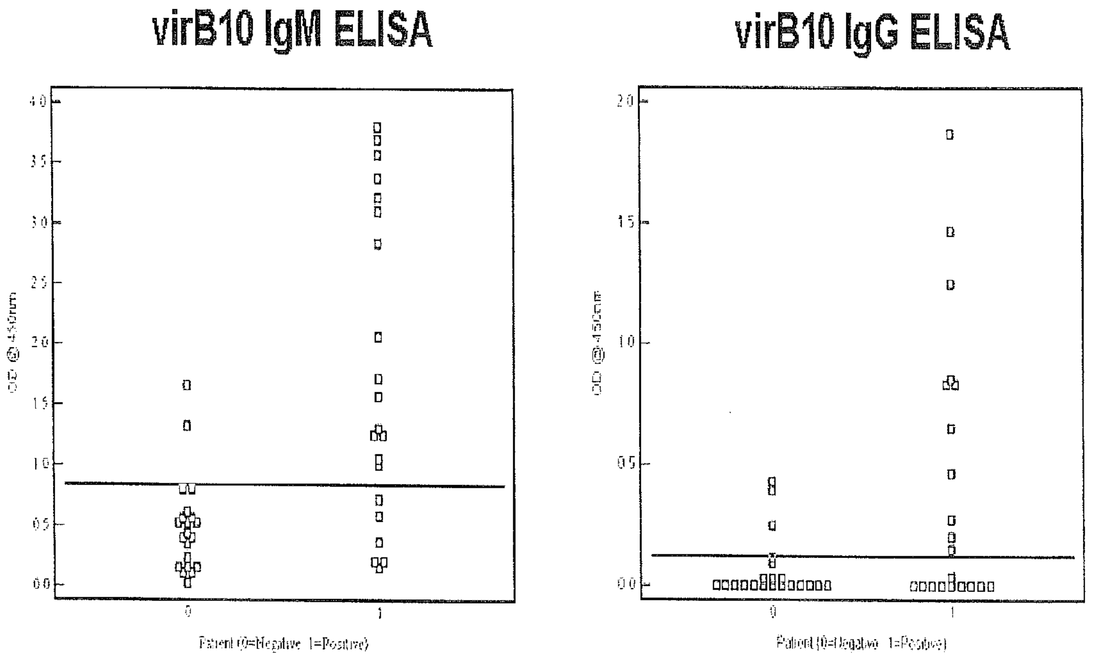
FIG. 17 depicts the IgM and IgG ELISA for Recombinant virB10 of *Anaplasma phagocytophilum.*

In this second series of studies, we examined recombinant virB10 in IgM ELISA. Recombinant virB10 protein exhibited a dose-dependent increase in binding towards IgM sero-positive serum (as measured by $OD_{450}$nm). IgM ELISA for recombinant virB10 attained a 71.4% sensitivity (FIG. 17) and 90.5% specificity, both of which satisfies the threshold (≧70%) required by industry.

Recombinant virB10 protein, when tested in an IgG ELISA, exhibited a dose-dependent increase in binding towards IgG sero-positive serum as measured by $OD_{450}$ nm. However, the binding levels attained (i.e., 52.4% sensitivity) were below the threshold (≧70%) levels required. IgG ELISA for recombinant virB10 has a specificity of 85.7%, which is within the acceptable range (≧70%) (See, FIG. 17).

Figure 17A:
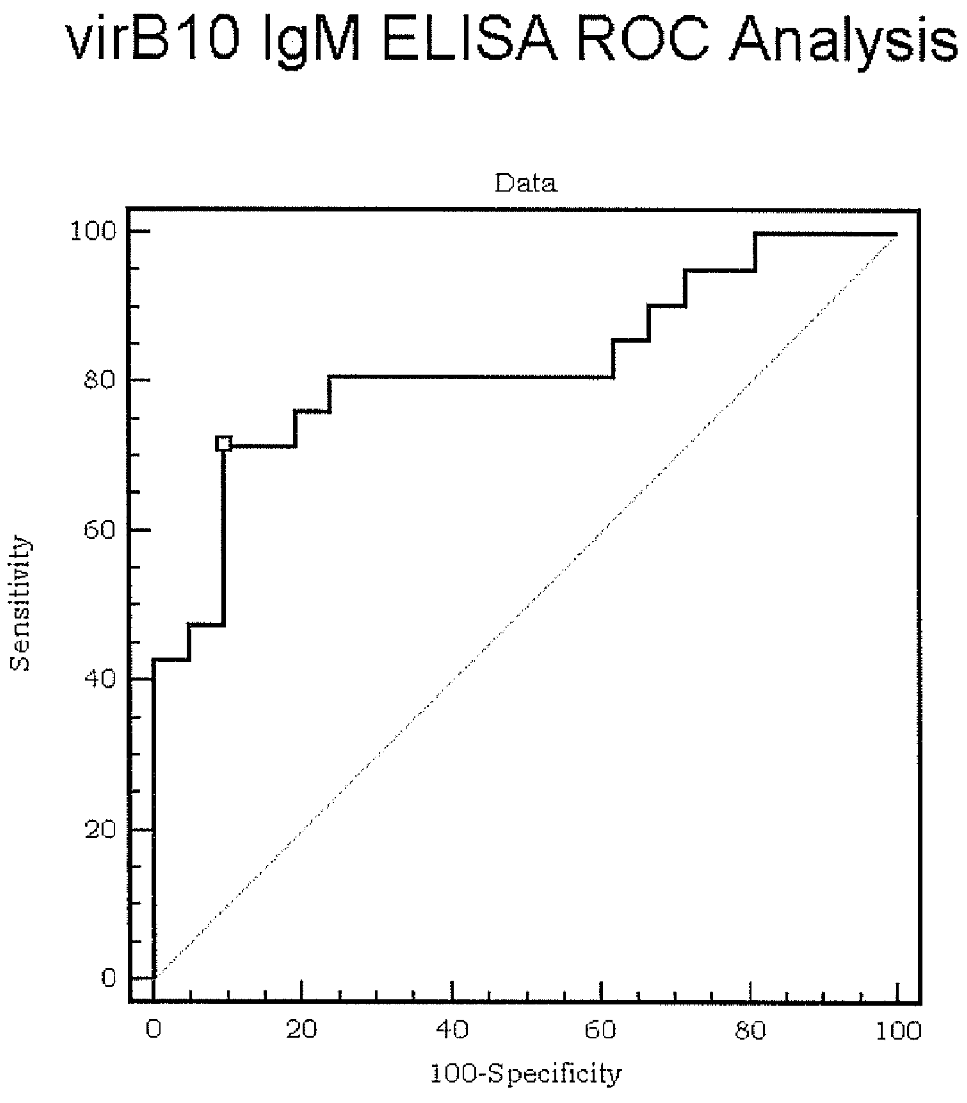
FIG. 17*a* depicts the ROC analysis for recombinant virB10 IgM ELISA.

The raw IgM ELISA data was analyzed with ROC curve determination using MedCalc statistical software. Performance analysis of ROC curve is shown in FIG. 17*a*. AUC of recombinant virB10 is 0.821 (95% confidence interval; range: 0.672-0.922).

c) Patient Study: virB11

In this third series of study, we examined recombinant virB11 in an IgM ELISA. As shown in FIG. 18, recombinant virB11 protein exhibited a dose-dependent increase in binding towards IgM sero-positive serum as measured by $OD_{450}$nm. The binding levels attained (i.e., 76.2% sensitivity) were within the threshold (≧70%) levels. FIG. 18 also depicts the IgM ELISA for recombinant virB11 having a specificity of 95.2%. Both sensitivity and specificity values were within the threshold (≧70%) levels.

Recombinant virB11 protein, when tested in a IgG ELISA, exhibited a dose-dependent increase in binding towards IgG sero-positive sera. The binding levels attained (i.e., 71.4% sensitivity). FIG. 18 also depicts IgG ELISA for recombinant virB11 having a specificity of 76.2%. Both sensitivity and specificity values were within the threshold (≧70%) levels.

Figure 18A:
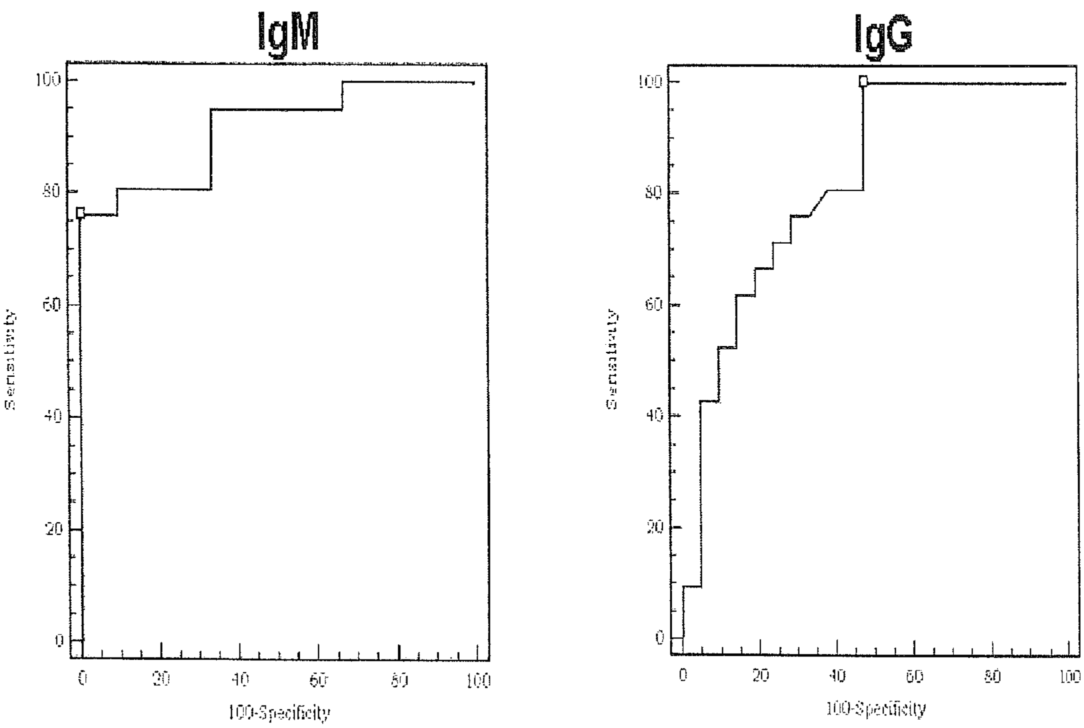
FIG. 18*a* depicts the ROC analysis for recombinant virB11 IgM and IgG ELISAs.

The raw IgM ELISA data was analyzed with ROC curve determination using MedCalc statistical software. Performance analysis of ROC curve is shown in FIG. 18*a*. AUC for recombinant virB11 ROC curve is 0.916 (i.e., 95% confidence interval; range: 0.788-0.979).

The raw IgG ELISA data was analyzed with ROC curve determination using MedCalc statistical software. Performance analysis of ROC curve is shown in FIG. 18*a*. AUC for recombinant virB11 ROC curve is 0.820 (i.e., 95% confidence interval; range: 0.670-0.921).

Experimental Protocol

*Anaplasma* IgG ELISA

1. Antigen coating concentration 0.5 μg/ml in carbonate buffer (pH 9.6) (100 μl per well). Coating overnight in 4° C.
2. Wash three time in PBST buffer (0.5% Tween-20)
3. Block with 200 μl blocker buffer (casein in PBS, Thermo Sci. #37528). Incubate for 1 hour in room temperature
4. Wash three times with PBST buffer (0.5% Tween-20)
5. Add 100 μl 1:200 diluted human sera (dilution buffer: 1:20 casein buffer in PBST). Incubate for 1 hour in room temperature
6. Wash four times with PBST buffer (0.5% Tween-20)
7. Add goat anti-human IgG antibody (1:15,000 diluted in casein dilution buffer (1:20 casein buffer in PBST). Incubate for 1 hour in room temperature
8. Wash four times with PBST buffer (0.5% Tween-20)
9. Add 100 μl TBM substrate. Incubate in room temperature for 3 minutes
10. Stop the reaction with 2N HCl
11. Read the result at $OD_{450}$

*Anaplasma* IgM ELISA

1. Antigen coating concentration 0.125 μg/ml in carbonate buffer (pH 9.6) (100 μl per well). Coating overnight in 4° C.
2. Wash three time in PBST buffer (0.5% Tween-20)
3. Block with 200 μl blocker buffer (casein in PBS, Thermo Sci. #37528). Incubate for 1 hour in room temperature
4. Wash three times with PBST buffer (0.5% Tween-20)
5. Dilute human sera in GullSorb™ (1:10) to prepare mixture 1. Incubate in room temperature for 5 minutes. Dilute incubated mixture 1 in sample dilution buffer (1:20 casein buffer in PBST). Therefore, the total dilution factor for human sera is 1:100
6. Add 100 μl 1:100 diluted human sera to the plate. Incubate for 1 hour in room temperature
7. Wash four times with PBST buffer (0.5% Tween-20)
8. Add goat anti-human IgM antibody (1:10,000 diluted in casein dilution buffer (1:20 casein buffer in PBST). Incubate for 1 hour in room temperature
9. Wash four times with PBST buffer (0.5% Tween-20)
10. Add 100 μl TBM substrate. Incubate in room temperature for 3 minutes
11. Stop the reaction with 2N HCl
12. Read the result at $OD_{450}$ All publications and patents cited in this specification are herein incorporated by reference in their entirety. Various modifications and variations of the described composition, method, and systems of the invention will be apparent to those skilled in the art without departing from the scope and spirit of the invention. Although the invention has been described in connection with specific preferred embodiments and certain working examples, it should be understood that the invention as claimed should not be unduly limited to such specific embodiments. Various modifications of the above-described modes for carrying out the invention that are obvious to those skilled in the filed of molecular biology, recombinant expression and related fields are intended to be within the scope of the following claims.

TABLE 1

| In Silico Analysis of Protein Components of Type IV Secretion System (TIVSS) in *Anaplasma phagocytophilum* | | | | |
|---|---|---|---|---|
| TIVSS Proteins | % Accessible Residues (Min/Max): Normalized from 0-1 | Average Flexibility (Min/Max): Normalized from 0-1 | Number of Antigenic Determinants | Cell Location* |
| virB3 | MIN: 0.230<br>MAX: 0.668 | MIN: 0.282<br>MAX: 0.671 | 6 | Inner Membrane |
| virB4 | MIN: 0.280<br>MAX: 0.716 | MIN: 0.278<br>MAX: 0.815 | 32 | Inner Membrane |
| virB6 | MIN: 0.279<br>MAX: 0.799 | MIN: 0.218<br>MAX: 0.944 | 30 | Inner Membrane |
| virB8 | MIN: 0.338<br>MAX: 0.730 | MIN: 0.347<br>MAX: 0.838 | 11 | Inner Membrane |
| virB9 | MIN: 0.372<br>MAX: 0.728 | MIN: 0.264<br>MAX: 0.778 | 13 | Outer Membrane |
| virB10 | MIN: 0.286<br>MAX: 0.827 | MIN: 0.236<br>MAX: 0.884 | 15 | Inner Membrane |
| virB11 | MIN: 0.340<br>MAX: 0.734 | MIN:0.398<br>MAX: 0.838 | 19 | Inner Membrane |
| virD4 | MIN: 0.248<br>MAX: 0.720 | MIN: 0.250<br>MAX: 0.866 | 26 | Inner Membrane |

*Cell Location is predicted based on PSORT analysis. See, *Bioinformatics* 21(5):617-623.

TABLE 2

| In Silico Analysis of Non-TIVSS Protein Components in *Anaplasma phagocytophilum* | | | | |
|---|---|---|---|---|
| Non-TIVSS Protein | % Accessible Residues (Min/Max): Normalized from 0-1 | Average Flexibility (Min/Max): Normalized from 0-1 | # of Antigenic Determinants | Cell Location* |
| Succinate Dehydrogenase, iron-sulfur subunit | MIN: 0.266<br>MAX: 0.697 | MIN: 0.380<br>MAX: 0.870 | 10 | Unknown |
| p44-Outer Membrane Protein | MIN: 0.266<br>MAX: 0.797 | MIN: 0.296<br>MAX: 0.870 | 10 | Outer Membrane |

*Cell Location is predicted based on PSORT analysis. See, *Bioinformatics* 21(5):617-623.

TABLE 3

| Oligonucleotide Sequences Used in Gene Amplification for *Anaplasma phagocytophilum* Encoding TIVSS and Non-TIVSS Protein Components | | | |
|---|---|---|---|
| Recombinant TIVSS & Non-TIVSS Protein | NCBI Accession # | Oligonucleotides | Gene Amplification |
| virB3 | YP_504978 | Fwd: 5'-gacgacgacaagatgtctggtagtgtaaaagcg-3' (Seq. ID No. 1)<br>Rev: 5'-gaggagaagcceggtctacatcacatcataggaattag-3' (Seq. ID No. 2) | Yes |
| virB4 | YP_504979 | Fwd: 5'-gacgacgacaagatgttaaagctaggttggtatcg-3' (Seq. ID No. 3)<br>Rev: 5'-gaggagaagcccggtctatgcattatcaccctttg-3' (Seq. ID No. 4) | No |
| virB6 | YP_504980 | Fwd: 5'-gacgacgacaagatgcatagggtagcaagggcattg-3' (Seq. ID No. 5)<br>Rev: 5'-gaggagaagcccggtctaactctgaccaccttttcc-3' (Seq. ID No. 6) | Yes |
| virB8 | YP_505898 | Fwd: 5'-gacgacgacaagatggtattggatatgtttggtc-3' (Seq. ID No. 7)<br>Rev: 5'-gaggagaagcccggtttatagaaattcatcatc-3' (Seq. ID No. 8) | No |
| virB9 | YP_505897 | Fwd: 5'-gacgacgacaagatgatgaatttctataaaaattttt-atg-3'(Seq. ID No. 9)<br>Rev: 5'-gaggagaagcccggtctaactaagagcctgattc-3' (Seq. ID No. 10) | Yes |
| virB10 | YP_505896 | Fwd: 5'-gacgacgacaagatggctgacgaaataaggggttc-3' (Seq. ID No. 11)<br>Rev: 5'-gaggagaagcccggtctacctcaccgcatcacg-3' (Seq. ID No. 12) | Yes |
| virB11 | YP_505895 | Fwd: 5'-gacgacgacaagatgactgggggtggtgcagctttag-3' (Seq. ID No. 13)<br>Rev: 5'-gaggagaagcceggtttacttattaccctctgaacactt-agtgaac-3' (Seq. ID No. 14) | Yes |
| virD4 | YP_505894 | Fwd: 5'-gacgacgacaagatgcatagttccaatcatatacg-3' (Seq. ID No. 15)<br>Rev: 5'-gaggagaagcccggtctactttagtcttccgttac-3' (Seq. ID No. 16) | Yes |
| Succinate Dehydrogenase, iron-sulfur subunit | YP_504786 | Fwd: 5'-gacgacgacaagatggtgcagttttctttgcc-3' (Seq. ID No. 17)<br>Rev: 5'-gaggagaagcccggtctagagctccaatccttttatc-3' (Seq. ID No. 18) | Yes |
| p44-8 Outer Membrane Protein | YP_504769 | Fwd: 5'-gacgacgacaagatgctaaggctcatggtgatgg-3' (Seq. ID No. 19)<br>Rev: 5'-gaggagaagcccggttcaaaaacgtattgtgcgacg-3' (Seq. ID No. 20) | Yes |

TABLE 4

| Recombinant Expression of TIVSS and Non-TIVSS Proteins in *Anaplasma phagocytophilum* | | |
|---|---|---|
| Recombinant TIVSS and Non-TIVSS Protein | NCBI Accession Nos. | Recombinant Expression |
| virB3 | YP_504978 (SEQ ID No. 21) | No |
| virB4 | YP_504979 (SEQ ID No. 22) | No |
| virB6 | YP_504980 (SEQ ID No. 23) | No |
| virB8 | YP_505898 (SEQ ID No. 24) | No |
| virB9 | YP_505897 (SEQ ID No. 25) | Yes |
| virB10 | YP_505896 (SEQ ID No. 26) | Yes |
| virB11 | YP_505895 (SEQ ID No. 27) | Yes |
| virD4 | YP_505894 (SEQ ID No. 28) | Yes |
| Succinate Dehydrogenase, iron-sulfur subunit | YP_504786 (SEQ ID No. 29) | No |
| P44-8 Outer Membrane Protein | YP_504769 (SEQ ID No. 30) | Yes |

TABLE 5

| IgM/IgG ELISA Assay for Recombinant TIVSS and Non-TIVSS Proteins | | |
|---|---|---|
| Recombinant TIVSS and Non-TIVSS Proteins | IgM ELISA | IgG ELISA |
| virB9 | Sensitivity = 61.9%-66.7%<br>Specificity = 85.7%-100% | No significant difference between positive and negative patient sera |
| virB10 | Sensitivity = 71.4%<br>Specificity = 85.7% | Sensitivity = 57.1%<br>Specificity = 76.2% |
| virB11 | Sensitivity = 76.2%<br>Specificity = 95.2% | Sensitivity = 66.7%<br>Specificity = 71.4% |
| virD4 | Not Determined | Sensitivity = 81.0%<br>Specificity = 42.9% |
| p44-8 Outer Membrane Protein | Sensitivity = 81%<br>Specificity = 90.5% | Sensitivity = 42%-71.4%<br>Specificity = 71.4%-100% |

What is claimed is:

1. A composition comprising:

(i) an isolated polypeptide, said isolated polypeptide is a recombinant polypeptide having an amino acid sequence selected from the group consisting of SEQ ID NO: 32 and SEQ ID NO: 33; and (ii) a support.

2. The composition of claim 1, wherein said support is selected from the group consisting of polyethylene, polypropylene and glass.

3. The composition of claim 1, wherein said support is a microtiter well.

4. The composition of claim 1, further comprising a packaging material.

5. The composition of claim 4, wherein said packaging material comprises an instruction for detecting the presence of antibody against *Anaplasma phagocytophilum*.

6. The composition of claim 1, wherein said isolated polypeptide consists of the sequence of SEQ ID NO: 32.

7. The composition of claim 6, wherein said isolated polypeptide is produced by a method comprising the steps of:

(i) introducing an isolated polynucleotide into a host cell, said isolated polynucleotide consists of the nucleotide sequence of SEQ ID NO. 26;

(ii) growing said host cell in a culture under suitable conditions to permit production of said isolated polypeptide; and (iii) isolating said isolated polypeptide.

8. The composition of claim 1, wherein said isolated polypeptide consists of the sequence of SEQ ID NO: 33.

9. The composition of claim 8, wherein said isolated polypeptide is produced by a method comprising the steps of:

(i) introducing an isolated polynucleotide into a host cell, said isolated polynucleotide consists of the nucleotide sequence of SEQ ID NO. 27;

(ii) growing said host cell in a culture under suitable conditions to permit production of said isolated polypeptide; and (iii) isolating said isolated polypeptide.

10. The composition of claim 1, wherein said isolated polypeptide is recombinantly expressed using an isolated polynucleotide.

11. The composition of claim 10, wherein said isolated polynucleotide is contained within a vector.

12. The composition of claim 11, wherein said vector is a plasmid.

13. The composition of claim 11, wherein said vector comprises a promoter of DNA transcription operably linked to said isolated polynucleotide.

14. The composition of claim 13, wherein said promoter is selected from the group consisting of lac promoter, trp promoter and tac promoter.

15. The composition of claim 11, wherein said vector is transformed into a host cell.

16. The composition of claim 15, wherein said host cell is *E. coli*.

17. The composition of claim 7, wherein said growing step comprises adding glucose prior to IPTG to said culture.

18. The composition of claim 9, wherein said growing step comprises adding glucose prior to IPTG to said culture.

* * * * *

SEQUENCE LISTING

```
<160> NUMBER OF SEQ ID NOS: 33

<210> SEQ ID NO 1
<211> LENGTH: 33
<212> TYPE: DNA
<213> ORGANISM: Anaplasma Phagocytophilum
<220> FEATURE:
<223> OTHER INFORMATION: Primer

<400> SEQUENCE: 1

gacgacgaca agatgtctgg tagtgtaaaa gcg                              33


<210> SEQ ID NO 2
<211> LENGTH: 38
<212> TYPE: DNA
<213> ORGANISM: Anaplasma Phagocytophilum
<220> FEATURE:
<223> OTHER INFORMATION: Primer

<400> SEQUENCE: 2

gaggagaagc ccggtctaca tcacatcata ggaattag                         38


<210> SEQ ID NO 3
<211> LENGTH: 36
<212> TYPE: DNA
<213> ORGANISM: Anaplasma Phagocytophilum
<220> FEATURE:
<223> OTHER INFORMATION: Primer

<400> SEQUENCE: 3

gacgacgaca agatgttaaa gctaggttgg tcttcg                           36


<210> SEQ ID NO 4
<211> LENGTH: 36
<212> TYPE: DNA
<213> ORGANISM: Anaplasma Phagocytophilum
<220> FEATURE:
<223> OTHER INFORMATION: Primer
```

-continued

<400> SEQUENCE: 4
gaggagaagc ccggtctatg catttttcac cctttg 36

<210> SEQ ID NO 5
<211> LENGTH: 36
<212> TYPE: DNA
<213> ORGANISM: Anaplasma Phagocytophilum
<220> FEATURE:
<223> OTHER INFORMATION: Primer

<400> SEQUENCE: 5
gacgacgaca agatgcatag ggtagcaagg gcattg 36

<210> SEQ ID NO 6
<211> LENGTH: 36
<212> TYPE: DNA
<213> ORGANISM: Anaplasma Phagocytophilum
<220> FEATURE:
<223> OTHER INFORMATION: Primer

<400> SEQUENCE: 6
gaggagaagc ccggtctaac tctgaccacc ttttcc 36

<210> SEQ ID NO 7
<211> LENGTH: 34
<212> TYPE: DNA
<213> ORGANISM: Anaplasma Phagocytophilum
<220> FEATURE:
<223> OTHER INFORMATION: Primer

<400> SEQUENCE: 7
gacgacgaca agatggtatt ggatatgttt ggtc 34

<210> SEQ ID NO 8
<211> LENGTH: 33
<212> TYPE: DNA
<213> ORGANISM: Anaplasma Phagocytophilum
<220> FEATURE:
<223> OTHER INFORMATION: Primer

<400> SEQUENCE: 8
gaggagaagc ccggtttata gaaattcatc atc 33

<210> SEQ ID NO 9
<211> LENGTH: 40
<212> TYPE: DNA
<213> ORGANISM: Anaplasma Phagocytophilum
<220> FEATURE:
<223> OTHER INFORMATION: Primer

<400> SEQUENCE: 9
gacgacgaca agatgatgaa tttctataaa aatttttatg 40

<210> SEQ ID NO 10
<211> LENGTH: 34
<212> TYPE: DNA
<213> ORGANISM: Anaplasma Phagocytophilum
<220> FEATURE:
<223> OTHER INFORMATION: Primer

<400> SEQUENCE: 10
gaggagaagc ccggtctaac taagagcctg attc 34

<210> SEQ ID NO 11
<211> LENGTH: 35

-continued

<212> TYPE: DNA
<213> ORGANISM: Anaplasma Phagocytophilum
<220> FEATURE:
<223> OTHER INFORMATION: Primer

<400> SEQUENCE: 11
gacgacgaca agatggctga cgaaataagg ggttc 35

<210> SEQ ID NO 12
<211> LENGTH: 33
<212> TYPE: DNA
<213> ORGANISM: Anaplasma Phagocytophilum
<220> FEATURE:
<223> OTHER INFORMATION: Primer

<400> SEQUENCE: 12
gaggagaagc ccggtctacc tcaccgcatc acg 33

<210> SEQ ID NO 13
<211> LENGTH: 37
<212> TYPE: DNA
<213> ORGANISM: Anaplasma Phagocytophilum
<220> FEATURE:
<223> OTHER INFORMATION: Primer

<400> SEQUENCE: 13
gacgacgaca agatgactgg gggtggtgca gctttag 37

<210> SEQ ID NO 14
<211> LENGTH: 46
<212> TYPE: DNA
<213> ORGANISM: Anaplasma Phagocytophilum
<220> FEATURE:
<223> OTHER INFORMATION: Primer

<400> SEQUENCE: 14
gaggagaagc ccggtttact tattaccctc tgaacactta gtgaac 46

<210> SEQ ID NO 15
<211> LENGTH: 35
<212> TYPE: DNA
<213> ORGANISM: Anaplasma Phagocytophilum
<220> FEATURE:
<223> OTHER INFORMATION: Primer

<400> SEQUENCE: 15
gacgacgaca agatgcatag ttccaatcat atacg 35

<210> SEQ ID NO 16
<211> LENGTH: 35
<212> TYPE: DNA
<213> ORGANISM: Anaplasma Phagocytophilum
<220> FEATURE:
<223> OTHER INFORMATION: Primer

<400> SEQUENCE: 16
gaggagaagc ccggtctact ttagtcttcc gttac 35

<210> SEQ ID NO 17
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 17
gacgacgaca agatggtgca gttttctttg cc 32

<210> SEQ ID NO 18
<211> LENGTH: 37
<212> TYPE: DNA
<213> ORGANISM: Anaplasma Phagocytophilum
<220> FEATURE:
<223> OTHER INFORMATION: Primer

<400> SEQUENCE: 18
gaggagaagc ccggtctaga gctccaatcc ttttatc 37

<210> SEQ ID NO 19
<211> LENGTH: 34
<212> TYPE: DNA
<213> ORGANISM: Anaplasma Phagocytophilum
<220> FEATURE:
<223> OTHER INFORMATION: Primer

<400> SEQUENCE: 19
gacgacgaca agatgctaag gctcatggtg atgg 34

<210> SEQ ID NO 20
<211> LENGTH: 36
<212> TYPE: DNA
<213> ORGANISM: Anaplasma Phagocytophilum
<220> FEATURE:
<223> OTHER INFORMATION: Primer

<400> SEQUENCE: 20
gaggagaagc ccggttcaaa aacgtattgt gcgacg 36

<210> SEQ ID NO 21
<211> LENGTH: 294
<212> TYPE: DNA
<213> ORGANISM: Anaplasma Phagocytophilum

<400> SEQUENCE: 21
atgtctggta gtgtaaaagc ggatcagctg tttaagggtt taaccaggcc caccatgctg 60
tttggtgtga gttatacgtt tgctattatg aatttcatgc tttcgatcat gatattcatg 120
tatagcaatg actttagggt attgtttatt ttagcgccag gtatgcacgg gttggggttt 180
attgcgtctg caaaggatcc tttgttcatg gatttgctaa tcataagaat gcagaagtgc 240
agtaagtgcc ttaatcggtt ctatcacaat tctaattcct atgatgtgat gtag 294

<210> SEQ ID NO 22
<211> LENGTH: 2406
<212> TYPE: DNA
<213> ORGANISM: Anaplasma Phagocytophilum

<400> SEQUENCE: 22
atgttaaagc taggttggtc ttcggctacg agaaagcgca agattgttaa tagggaatac 60
catcagtcga actttttgcc atatcaggag cactggaata gcactactct tgttacgaag 120
gatggttcgt tgcttaaggt aatcaagctt tcaggctacg ctttcgagac agcagatgat 180
gaagatcttt ctatacaaaa ctcgatcagg aatcagactc tgcgaagtat gtcgtctgcg 240
gcgtttggtc tgtattttca cattataagg cgcaggcgga acgcgttttc tgagggtttt 300
gctggtaagc aattttctag tgcgtttgct gatgctgtga atatgcagtg gcgcaataag 360
catatgacca agcaatcttt cacgaatgat ctttatataa cgattgtgag ggaaggtagt 420
aataaaagta ccgagctatt cgttaatcta ttacaaaaaa tcaacaaaaa ggcagcgact 480
gagagttgga aaaacgatat gcgggctgct tttgaggatt tagaggaggt taccaatcgg 540

-continued

```
gtagtcacta gcttgcgtaa ttatgcgcct agggaattgg gtattaggag tactccggct    600
ggggattttt cagagattat ggagtttttg ctccagattg tgaattgcgg tgcagtgcat    660
aatgttgcgg tagatcttgg tgatatttct aaatatctac ccatgcacag gttgtatttt    720
ggtcataaag ttgtgcaggt agtctgtcat gatggttcga aatacgctgg tttaattagt    780
ctcaaggagt acgggcagac gacttcagct gggatgttgg atgcgttttt gcagttacct    840
tatgagttta taataacgca gtcgtttaag tttaccaatc gtcaggctgc tattacaaag    900
atgcagattc agcagaatcg aatgatacag tcttcggata aggctgtatc tcagatttat    960
gaaatctcta aagcgcttga tgatgctatg agtggtaaga tagcttttgg gcatcatcat   1020
ctcactgttt tatgcataga gaaaactccc aagaatttgg aaaatgctct ctctttagta   1080
gaagcagagt tgtcgaattg tggggtatat cctgtaagag aaaaagtgaa tctagagccg   1140
gcattttggg cgcaattgcc tggtaatttc tcttatgttg tacgtaaagc tgtaataagt   1200
actctcaaca tggcaggttt tgcgtcgcag cataactatc caagtggcca gaaatttggc   1260
aatcactggg gagaagcggt tactgtattt gatacgacgt caggcacgcc gttctttttc   1320
agttttcaca tgcgtgatgt tggcatacaa gcaatcattg ggccaactgg tgcgggaaag   1380
acagtactga tgaacttttt gtgtgttcag gcgatgaagt ttctccgcg  ggtgttcttt   1440
tttgacaaag atcatggtgc tgagatattc atcagggctt tgaagggggt atacagcatt   1500
atagagacaa gaggctccac tgggttaaat ccgctgcact tagacgatac tcctgacaat   1560
aggggtttc  tcatggagtg gtttaagtta ttggctacta ctctgtcaga taagcttacg   1620
cctgacgata tattgcgcat tgatgatgct atagagggta atttcaagct caaaaaggaa   1680
gacagaaagt tacgtaatct ggttcctttt ttgggtatag gtggagaaga tactctagcg   1740
agtcgcatga tgatgtggca ttcagaaggg tcgcacgcgg cgctttttga taatgacgaa   1800
gatgtattag acttcactaa gtctagagta tttggatttg agatgggata tttgctaaaa   1860
gatcccatgg ctcttgctcc gacgcttttg tatttgtttc acaagataag tatttctctc   1920
gatggaactc cttctatgat tatcttggac gaagcgtggg cgctgataga taatcctgtt   1980
tttgcgccta ggattaaaga ctggctaaaa gttcttagga agctcaatac ttttgtcata   2040
tttgcgacac agagtgttga ggatgctagt aaaagtcaga taagtgatac cttagttcag   2100
cagactgcca ctcagatatt tttgcctaat cttaaggcta ctagtgctta cagggatgtt   2160
ttcatgctga ctgagcggga gtattcttta ataaaatata cagatcctgg cactaggttt   2220
ttcctagtca agcagggggt cagtgctgtt gtggccagga tagatttacg agggctcgat   2280
gacacgataa acgttttgtc aggtagggcc gagaccgttg ccatacttcg tgaaattatg   2340
gaagaagtag gggatgatcc aaatgtgtgg ttgcctattt tttatcaaag ggtgaaaaat   2400
gcatag                                                              2406
```

<210> SEQ ID NO 23
<211> LENGTH: 2541
<212> TYPE: DNA
<213> ORGANISM: Anaplasma Phagocytophilum

<400> SEQUENCE: 23

```
atgcataggg tagcaagggc attggtattt ttgatgtttc ttgttgttac agttccttta     60
acgtcatacg cggcgggcga tgctactgct agtacaccaa cagaggaaga aaacaacttg    120
gtgcattata gacacgcgga ggctactaat ccgcgttgtg gtgctgtgga agagcttgca    180
aagataggta gcattggaat aactgcagcg ctcggtggtg gtgttgtagg ggtgggtttt    240
```

-continued

```
ctatatgttc cgattgttgg atttaggcct ctcggttttg caatgatagc tgcttcgatt    300
gcaacaatct cagctggtat tgctgcgtca gcaccgtatt ttgcatgtaa ttggagtttt    360
gtccgtcatc ccgtgttgcg ctttgaaagc gctgatgatg tttcgcgcgc agctggcggt    420
gaagtgccta cggagggtga ttataaggag tgtgctgaac cagtagctgc gtcagaaatt    480
ttaggaaaat acggagggga ttgtagcaaa gaatttgctt acatggctga ttattatgcc    540
tgtttagcag aaagcaagag tttagaggat gctcggaagg cagagcctac atgtccaagt    600
aagaagttta agaaggcgag taattatgca tggcctaaga atcgggtatc tagttcacgt    660
tatatagaag tttgttatcg tcatcctttg ggcacggtgt atatgtcgcc ttatgttgcg    720
gcgcgtctag gatttgcagg tagagatcct aaagaagttt taaaggagag taagtacccg    780
cgggaagcta catttggtga taatcatatg cacaatacaa agcttgctgt gtcgggagct    840
tggactgagt ttgagtatac gattcagtgt aaagttctaa aagctggtca ggaggctaaa    900
ctgcatgatg cgacttttag agctgtagaa cggggtgcga agctttgtgt tgacgctgtt    960
aaactaagtg gtgtgccatt tatggctaag ccagagatcg ggtgtcagat gcgtcctaat   1020
tcacctccgg cgcctatgtg tgctaagtct gtgcaaaggg agactaaggc cgctgatgga   1080
agtaagatta ttagctatga caatagtgga tgttatagct gttatgttgc cgagacttgt   1140
aaaggtgtag caaatttaaa ttccaggtct attttcccta taacgtcggt ggttgtggga   1200
tgcatagttg attctctgaa aaatctgcta gatcctcctg cagattgtac ggggcgcgca   1260
agggcaatga attcagtaaa tcctggattt ttgaaggttg ctcaggagaa gcttaagaag   1320
acagtgatgg ctgctttgat acttgcattg gtgttgtttt caattaaggc agttttgggt   1380
ggggtacaaa gtgcagggga gctttatatg accgttataa agtttgctct ggtgatttat   1440
ttcacccaag gtgacgccat gtcccttgct tacgaatatt tgactaagct ttctataggg   1500
ctttcagaca ttgtgctgcg tgcagctgga ggtgatactg gaatttgtga ctttcaagca   1560
tcggattata gtccgcagta cttatatctc atgccatggg ataggctgga ctgtcgcatg   1620
atgttttacc taggtagtca attaacaggg ggtacaggaa caggtattct gcttactgta   1680
ttgttaacag cggggctatt aataccagct atattaatta atgcgaaggt cataatatgc   1740
ttagtggcgt ttttcgccgt cattatgctg gtacttacga ttatatggac ggtatatgtt   1800
ttcttgttgt cgctgatagc attgactgtg ctaacgataa tctctccact tatgatccca   1860
atgtctttat ttcaggctac aaaggggttt tttgatgggt ggactaggca gttaatgacc   1920
tattctctct atcctgtgat attgtttgcg tttctttctt tgatgtttgc tgtttttgat   1980
aatctatatt ttggtgaatt aaaatttcat cgtgggggaa gtgacggcac ggtagctggt   2040
gctcccaaag cagggcagaa aatatggttt gagcttgtag acaagaaggc atgtgagaag   2100
cgtgaaaatg aaacaaatct agcgtgcata tttgacacaa tgcagttttt tagtaggccg   2160
ttggtgtttg gtatttctgt taatgcgccg gaatttaaaa tggctactac tgctcagata   2220
tggactaaat tgggagtatt cgtactaatt ggatttttgt tttatcactt tttaggttct   2280
atatcgtaca ttgctgggga gcttgctggg gatccgagag ctggtgttat aggtagtggt   2340
ggtatgaacc cgcgtagtat tgctcataaa gcagcgggta tggcttctgc agttagggga   2400
gctgcttcgg gtaaactttc agatttgggc tccaaggctc gtgatgccat aaaaggtatt   2460
ggttcctctg atagtggagg tacagataag gtttctgggg gaagcagtgg aggagattct   2520
ggaaaaggtg gtcagagtta g                                             2541
```

<210> SEQ ID NO 24
<211> LENGTH: 717
<212> TYPE: DNA
<213> ORGANISM: Anaplasma Phagocytophilum

<400> SEQUENCE: 24
ttatagaaat tcatcatccg ccctatagta agtgatctgg aagcccaaag ggttcacctg 60
tctatcttgt tcagtcatct caagagagga atacctaaag gaaagagtag caattctatc 120
tctctttaca atcgagccgc tatgattaac gaattccata gtaaaccgca cctgaacctg 180
ccctccttct agatgttgca gagagcgcac ttttagagct cctgatacaa catccgaata 240
aagcgtcata ggactagaag ggttactagg acgtatccaa ctacgaaact cgctataggt 300
ttcttgggac gaaaggagac gtactctcgt atagtagtta tactggaaat tgttgggatc 360
atagagctca cgagccttta tgtactccac tataaaataa ttacttaata cctcgtcggc 420
agaatactgt tttacagtca tcgggtttac tagcgttgta atccctgact tcttttctat 480
ttctacaacg aagggttcta ttgttcttgt tttccctatt ctgaaaatga cgaaagtact 540
tacagcgata caaaataccg acaacactac aagaagaagg agtatattgc gctgcacgac 600
cacggaaccg tatctgtcat gataccaatc tccgatcttt cccgacacgc aatcgcgctc 660
agaacctgtc acgggctttt ttttttcctt tccaagacca aacatatcca ataccaa 717

<210> SEQ ID NO 25
<211> LENGTH: 846
<212> TYPE: DNA
<213> ORGANISM: Anaplasma Phagocytophilum

<400> SEQUENCE: 25
atgatgaatt tctataaaaa tttttatgtt gctttggtaa cggctttcgc gctgttctct 60
atgagtaaag catgctttgc cagcacaaat attggcgtac cagtttctgt agatagtaga 120
ataaagacat ttgtctacag tcagaatgag gtttttccgg ttgtgttcaa ctatggctat 180
cattcctaca tagaattctc gcaaggtgag acggtgcgag ttatggcttt aggagataat 240
gcaaattgga agataaggcc ggtggacaac aagttatacg tcatgccctt ggaaaaagag 300
gggcacacta atatgctcat agaaacgagt aaggggcgga gttacgcttt tgatttgata 360
tcgactgcga ttcctctgag tggaggtgct gcatctagta ttaacaagtt gggaaagact 420
aattctgcat tagcagactt agcttatgta gtgcgttttt actatccgca gagtgataga 480
aattttgata tcatgggaca gaaacttgag atatctcctc ctagcctggc tagcagttta 540
gatgctgatg atgtggaaat agagccaaat gccactagaa ccaactatat gtttactggt 600
ggaagtgctc acgtttctct agctcctacg caggcttttg atgatggata tctgacatac 660
tttcagtttg gtaaaaataa caaagaaatt cccaaaatct acgttgtgaa gaaggatgga 720
aaaaaagttc catgtaaaat gctgcttctt agggactatg taatagttga gggggtgcat 780
gagctgtttt accttgattt tggtgatggc aggagtgtag aagttgtgaa tcaggctctt 840
agttag 846

<210> SEQ ID NO 26
<211> LENGTH: 1305
<212> TYPE: DNA
<213> ORGANISM: Anaplasma Phagocytophilum

<400> SEQUENCE: 26
atggctgacg aaataagggg ttctagcagc ggggagaaca ttgaggataa tgttaatgta 60
gtaggtgtag caaagagtaa gaagctcttt gttatcatag tggtgctgat tgctactgga 120

-continued cttatgtact atttttcttt cttcaataag gagtcttcgg ataatgagga agatactcag 180
attcctcgtg ttatcgaaga gaaggaagta gaaaaattga ggaaggatgc gggaaggccg 240
gctcaggaga ctgctcctag aatcttgacg ccaccaccga ggttgcctga gttgccgccg 300
cttgtaatgc ctactgtacc tgatattcct gtggtaacaa aattgcttaa gccgcctgta 360
gaggaggagt ttgttgaaga gtataacgtt caagaggttc cttcaccaat gggtaatatt 420
gctcctcctg aacgcgagga gatatcttta cctttgccgt ataagacgat aacaactgag 480
cagccgtcgt ttctggggta tgataaagaa aaaagaggag cccctatgat cgcatttggt 540
ggcggtggtg gcgaagctgc tggtagtgaa tccggtgatg gttctgttgg cgggaaggaa 600
gatgctcggt ttactgcgtg gcaagggtta gagggtactc aatctcctag tgttagagcg 660
acaagagtgg gggatacgag atatataata ctgcaaggtc acatgattga tgctgtttta 720
gagacagcaa taaactcgga tatttcaggg gtgctcaggg ctgtggtatc cagagatgta 780
tatgcttctt ctggagatgc ggttgtaata ccgaaggggt ctaggcttat tggtagttat 840
ttctttgatt ctgctggtaa caatgtaagg gttgatgtta attggtccag ggtcatttta 900
cctcatggcg ttgatataca gatagcgtct agtggaactg atgaactagg aagaaatggt 960
atttctggtg ttgtagataa taaagtgggc tccatattga cctctactat ctttttggcg 1020
ggtatatctt tggggacagc ttatgtgacc gagcagatac cgtcgttgcg gactgagact 1080
gttaaggttg agactcctgc ggatggtaaa gacgggaaga aaactacttc atcatctctt 1140
tcaacaaaga tagtttctga tgctattaag gatttctctg actctatgaa agagattgtg 1200
aataagtatt ctaataggac tccgactgtc tatgtagatc agggtactgt gatgaaggta 1260
tttgtgaatc aggacgtagt atttcctcgt gatgcggtga ggtag 1305

<210> SEQ ID NO 27
<211> LENGTH: 999
<212> TYPE: DNA
<213> ORGANISM: Anaplasma Phagocytophilum

<400> SEQUENCE: 27
atgactgggg gtggtgcagc tttagaaact tatcttgaac cgcttcggga tatatttgct 60
gaagaaggag taaatgaaat atcaataaat aactcatgtg aagtatgggt tgaaaatagg 120
ggaaatatta ggtgcgagca tattgcagca ttgacgactt ctcatctcag gggttaggg 180 cgtcttattg ctcaggctac ggagcaaaag ttaagtgagg aaacgccact gctttctgcg 240
tctttaccca acgggtttcg tgtacaggta gtttttcctc cggcatgtga gggtgataag 300
atagtgatgt cgattcgtaa gccttctgcg atgcagttgt cgcttgatga ttatgaaaaa 360
atgggggcat tttctcatgt tgctcagcag aatgacaagc tcagagatga aaatagcgaa 420
ttaggtgagt tgctatctaa gggtaaaata aaggaatttt tagaaacggc ggtacaaaaa 480
aagaagaata taattgtgag tggtggtacc tctacaggga agactacatt tactaacgct 540
gccttgagag ctataccttt agaagagagg attattactg ttgaagactc gagggaaatt 600
gtcctatctc atccaaatcg cgtacattta cttgcttcta aaggtgggca aggtagagca 660
cgtgttggta cgcaagattt gatcgaagca tgtcttcgtc ttcgtccgga taggattata 720
gtgggggagt tgaggggtgc tgaagccttt agtttttga gggctattaa tactgggcat 780
cctggatcta tttctacgtt gcacgctgat actccaagga tggctataga gcagttaaag 840
cttatggtaa tacaggcagg aacgggatta ccagcagatc agattgtgaa ttacataatg 900
aatattgtgg atgtgatagt gcagctgaag aggagctctg gtggagtgcg ccatgtttca 960
gacattttgt tcactaagtg ttcagagggt aataagtaa 999

<210> SEQ ID NO 28
<211> LENGTH: 2223
<212> TYPE: DNA
<213> ORGANISM: Anaplasma Phagocytophilum

<400> SEQUENCE: 28
ctactttagt cttccgttac tgctatcatt gtcatcagta ggtcgatctt ctccaaattc 60
atcctcttct tctaaagaat catcttcttc aaagtcttcg tcctcctctg gctctaagct 120
atcaaactcg tcgtcaacaa cctcatcatc taaaagctca tcctcaaaag cttcattctc 180
atcccaatct ccgtcccctt ctaactccat gtcatcttca taaggatcgt cgtagtcttc 240
atcattaaga acatcatctt cgtcgtgaaa gtaatcatca gactcatcca agtcctctaa 300
atcatcttca ggttcttcac ctataccgta taggtcttca aattcttctc tgtccacaag 360
atcaccatca tcttcatatc catattcagc acgctcagga ggattttctg cactagaact 420
acccatcaac gcctttagat cttcactatt ctccgaagcc tcagacacaa tacctgcttc 480
cccctcgact ccaccacgaa tcttttcagg atcgtacggc tcttgcgtag gaataaacgt 540
gctcttcaat agcctacgcg taaacgtttt atcttcaaag tactttattt ttctagactt 600
tatcggataa gtagattcaa ttaagagaat ttgctcatcc ttaggtaaca ttataacttc 660
ctgaggcaac aacaacgccc gctgtgtatc agaaatatgc agtgagcgtg aagcaggatt 720
aaggtctaaa aacttaggcc tatttagaga ctcctgactc acggtcttat ttccaataag 780
ttgcgatatc aagtttgcag tctctatgtt gtttgcagca aaagttatac ggtaagtaga 840
attagatagg aaagagttca tccctgcttc ttcgtatatt ccctttaact gttctgtatc 900
ttgtattatc aaaaataatc ttaccctgta cccacgaaag taagctatcc ccgtctggaa 960
ctgctccatc tttccaagag ttggaaactc atccatcaaa aacaatacac cataaggttc 1020
atcatcagaa ggtagagtac gacataaaaa ctccgttgcc tgttgataaa aaacctgcat 1080
caaaggcctt aacctagtga gattatcagg tgtaactcca acatacacag aaacacgctt 1140
cctcttgaaa tcttgtatat taaaatcact agaagctgtt gcagtatcaa taagagggtt 1200
agcccacaat tccaaagaag agttcatggt agaaataaca ccagaacgtt ccttatccgc 1260
cttctgcaag aatgcagcaa tgttcatgta cgcaacaggg tgtattttct tacctatcgt 1320
gtccaataca accgcaaggt tatatactac gtcatcgcta cgcattgttc ttacaacttc 1380
gccaaatgac ttaacctttt ccggaactgc caataaatag agcaccaccc caacaaataa 1440
actccttgct tcgttgtacc aaaagtcttg ctccggcatg ataaggttag caatcttctg 1500
tacgtcatct accatctgcc caggtttttt gcttatccaa tccagcggat tataacaatg 1560
actgatacca tctggctgcg caggattcca tacatatact tcctgcccaa ttttcttacg 1620
ccaaccactc gtgaggtcgt agttttcaag cttcacatca tgcacaatta cagaatcttc 1680
ccagaataaa agattgggaa ttacaaaccc tacaccttta ccagacccag ttggagcaaa 1740
aagaagagca tgttgatagc catctgctac caaataaccc ctctgatctt tccctaataa 1800
aattccacgt ctgctgcgta accctatttt tctaatatcc cgctctgaag cccaccgaga 1860
atctccgtgt aaagattctt tcttcttaaa aggtcgccaa tcaataagaa catgtcgaag 1920
attccacgcc acaagacaaa caagaccaat aggagcaaaa aatgaacccc acaactttag 1980
cgaattagca attccaaaca gcttgggatc cccccaccat ttactaatat actgaaaaat 2040
agtcggccac agccgcatgg gaaaatctga cacactgggg tttattgcat taaaatctaa 2100
ataatctact ccccatacaa gaagcacaaa taatacgcca gaaatataaa agcaaaactc 2160
caacaggcaa aacagcccac aaaagaatac caaaatattt cgtatatgat tggaactatg 2220
cat 2223

<210> SEQ ID NO 29
<211> LENGTH: 789
<212> TYPE: DNA
<213> ORGANISM: Anaplasma Phagocytophilum

<400> SEQUENCE: 29
atggtgcagt tttctttgcc aaaaaactcc aagataaacc cgaatggtaa ggtatacaat 60
gctacggagg gtgctaagcg cactggatgt tttaagatat ataggtggtc acctgatgac 120
ggagagaatc cgaggattga tacctactat atagatttgg acaaatgtgg gcagatggtc 180
cttgatgcgc taattaaagt taagaatgag tatgactcga ctttgacttt taggaggtca 240
tgtcgtgagg ggatatgtgg atcgtgtgcg atgaatatag atggcacgaa cactttggca 300
tgtacgaagt atatttctga tattaaggga gatgtgaaaa tatttccctt accgcatatg 360
gatgttatca aagatttggt gccggattta agtaattttt acaagcaata taagtctata 420
agtccttggt tgaagtctga tggtgcgagg tctgataggg aggagcatct tcagagcata 480
gaggacagga gtaagttgga caaggtatac gattgcattt tgtgtgcgtg ttgtagtaca 540
agttgtccga gttattggtg gaatccagat aagtatttgg gacctgcggc gttgttgcag 600
gtatacaggt ggttggttga tagtagggat acggcgacag aggagcgtct tgcgttttta 660
gaggatgctt ttaagttata caggtgtcat actatcatga attgtactaa gacttgtccc 720
aaggatctga atcctgctaa ggcgatagcg aaaataaagc agatgatgat aaaaggattg 780
gagctctag 789

<210> SEQ ID NO 30
<211> LENGTH: 1008
<212> TYPE: DNA
<213> ORGANISM: Anaplasma Phagocytophilum

<400> SEQUENCE: 30
tcaaaaacgt attgtgcgac gtgagccatc aacaacaccc acgaagttac cccctaaacc 60
aacacaagca taaggaacaa cacctaaacc ttcactaaga agatcataac aagcattgac 120
cattacagaa gtagaagaaa ccgccctgat ctcaacaact tcaccccctt caatagtctt 180
agctagtaac cctgctacta tggtttttttc ttcggaagtg agttttgtta gatctttcgc 240
tacggcgtct gcattgtcgt ttttattatc agatggcgct ccatcatttt tcgtagatgt 300
cggccaattc ttactaccat tttccaaaag agttttcttt ataaaatgct cgaaaacctc 360
tgcgttgtta ctactaccgc tatgacttcc cccatcatca ctacataacg atgtattgtt 420
gtcactgctc ttcgtaccgg ttttatcagc atacttacca tactttccag aactttgggc 480
tttcgtcgca caaaccttct tatcaatacc gggatgagaa accacaaccg ccttagcaaa 540
ctgaacaaag tctttacccg aagttttggc aagagcagca gcaaggttat cagtctgtcc 600
agtaacaaca tcataagcta actccttagc tagtagatat actgtatcag cttcatcttc 660
cttactacca ctatctctaa tacccttggt cttgaagcgc tcgtaaccaa tctcaagctc 720
aaccctggca ccaccaatac cataaccaac actaccttcc atagctacaa gcatgttgtc 780
cttaaaccca atccgaggat caggtgtgtt ccagtcaaac ttgttagact ctagctttac 840
actctttcca tcctttaagt atggatatac tgccttagtc tctccgttac tctcccttat 900
actaaaatct cttatcttgc taaacgctgg actgtaatcc aagccaacat agaaatatcc 960
cgctctacca gaccctgaa gcactaccat caccatgagc cttagcat 1008

<210> SEQ ID NO 31
<211> LENGTH: 281
<212> TYPE: PRT
<213> ORGANISM: Anaplasma Phagocytophilum

<400> SEQUENCE: 31

Met Met Asn Phe Tyr Lys Asn Phe Tyr Val Ala Leu Val Thr Ala Phe
1 5 10 15

Ala Leu Phe Ser Met Ser Lys Ala Cys Phe Ala Ser Thr Asn Ile Gly
20 25 30

Val Pro Val Ser Val Asp Ser Arg Ile Lys Thr Phe Val Tyr Ser Gln
35 40 45

Asn Glu Val Phe Pro Val Val Phe Asn Tyr Gly Tyr His Ser Tyr Ile
50 55 60

Glu Phe Ser Gln Gly Glu Thr Val Arg Val Met Ala Leu Gly Asp Asn
65 70 75 80

Ala Asn Trp Lys Ile Arg Pro Val Asp Asn Lys Leu Tyr Val Met Pro
85 90 95

Leu Glu Lys Glu Gly His Thr Asn Met Leu Ile Glu Thr Ser Lys Gly
100 105 110

Arg Ser Tyr Ala Phe Asp Leu Ile Ser Thr Ala Ile Pro Leu Ser Gly
115 120 125

Gly Ala Ala Ser Ser Ile Asn Lys Leu Gly Lys Thr Asn Ser Ala Leu
130 135 140

Ala Asp Leu Ala Tyr Val Val Arg Phe Tyr Tyr Pro Gln Ser Asp Arg
145 150 155 160

Asn Phe Asp Ile Met Gly Gln Lys Leu Glu Ile Ser Pro Pro Ser Leu
165 170 175

Ala Ser Ser Leu Asp Ala Asp Asp Val Glu Ile Glu Pro Asn Ala Thr
180 185 190

Arg Thr Asn Tyr Met Phe Thr Gly Gly Ser Ala His Val Ser Leu Ala
195 200 205

Pro Thr Gln Ala Phe Asp Asp Gly Tyr Leu Thr Tyr Phe Gln Phe Gly
210 215 220

Lys Asn Asn Lys Glu Ile Pro Lys Ile Tyr Val Val Lys Lys Asp Gly
225 230 235 240

Lys Lys Val Pro Cys Lys Met Leu Leu Leu Arg Asp Tyr Val Ile Val
245 250 255

Glu Gly Val His Glu Leu Phe Tyr Leu Asp Phe Gly Asp Gly Arg Ser
260 265 270

Val Glu Val Val Asn Gln Ala Leu Ser
275 280

<210> SEQ ID NO 32
<211> LENGTH: 434
<212> TYPE: PRT
<213> ORGANISM: Anaplasma Phagocytophilum

<400> SEQUENCE: 32

Met Ala Asp Glu Ile Arg Gly Ser Ser Ser Gly Glu Asn Ile Glu Asp
1 5 10 15

Asn Val Asn Val Val Gly Val Ala Lys Ser Lys Lys Leu Phe Val Ile
20 25 30

```
Ile Val Val Leu Ile Ala Thr Gly Leu Met Tyr Tyr Phe Phe Phe Phe
        35                  40                  45

Asn Lys Glu Ser Ser Asp Asn Glu Glu Asp Thr Gln Ile Pro Arg Val
    50                  55                  60

Ile Glu Glu Lys Glu Val Glu Lys Leu Arg Lys Asp Ala Gly Arg Pro
65                  70                  75                  80

Ala Gln Glu Thr Ala Pro Arg Ile Leu Thr Pro Pro Pro Arg Leu Pro
                85                  90                  95

Glu Leu Pro Pro Leu Val Met Pro Thr Val Pro Asp Ile Pro Val Val
            100                 105                 110

Thr Lys Leu Leu Lys Pro Pro Val Glu Glu Glu Phe Val Glu Glu Tyr
        115                 120                 125

Asn Val Gln Glu Val Pro Ser Pro Met Gly Asn Ile Ala Pro Pro Glu
    130                 135                 140

Arg Glu Glu Ile Ser Leu Pro Leu Pro Tyr Lys Thr Ile Thr Thr Glu
145                 150                 155                 160

Gln Pro Ser Phe Leu Gly Tyr Asp Lys Glu Lys Arg Gly Ala Pro Met
                165                 170                 175

Ile Ala Phe Gly Gly Gly Gly Gly Glu Ala Ala Gly Ser Glu Ser Gly
            180                 185                 190

Asp Gly Ser Val Gly Gly Lys Glu Asp Ala Arg Phe Thr Ala Trp Gln
        195                 200                 205

Gly Leu Glu Gly Thr Gln Ser Pro Ser Val Arg Ala Thr Arg Val Gly
    210                 215                 220

Asp Thr Arg Tyr Ile Ile Leu Gln Gly His Met Ile Asp Ala Val Leu
225                 230                 235                 240

Glu Thr Ala Ile Asn Ser Asp Ile Ser Gly Val Leu Arg Ala Val Val
                245                 250                 255

Ser Arg Asp Val Tyr Ala Ser Ser Gly Asp Ala Val Val Ile Pro Lys
            260                 265                 270

Gly Ser Arg Leu Ile Gly Ser Tyr Phe Phe Asp Ser Ala Gly Asn Asn
        275                 280                 285

Val Arg Val Asp Val Asn Trp Ser Arg Val Ile Leu Pro His Gly Val
    290                 295                 300

Asp Ile Gln Ile Ala Ser Ser Gly Thr Asp Glu Leu Gly Arg Asn Gly
305                 310                 315                 320

Ile Ser Gly Val Val Asp Asn Lys Val Gly Ser Ile Leu Thr Ser Thr
                325                 330                 335

Ile Phe Leu Ala Gly Ile Ser Leu Gly Thr Ala Tyr Val Thr Glu Gln
            340                 345                 350

Ile Pro Ser Leu Arg Thr Glu Thr Val Lys Val Glu Thr Pro Ala Asp
        355                 360                 365

Gly Lys Asp Gly Lys Lys Thr Thr Ser Ser Ser Leu Ser Thr Lys Ile
    370                 375                 380

Val Ser Asp Ala Ile Lys Asp Phe Ser Asp Ser Met Lys Glu Ile Val
385                 390                 395                 400

Asn Lys Tyr Ser Asn Arg Thr Pro Thr Val Tyr Val Asp Gln Gly Thr
                405                 410                 415

Val Met Lys Val Phe Val Asn Gln Asp Val Val Phe Pro Arg Asp Ala
            420                 425                 430

Val Arg
```

<210> SEQ ID NO 33

-continued

```
<211> LENGTH: 332
<212> TYPE: PRT
<213> ORGANISM: Anaplasma Phagocytophilum

<400> SEQUENCE: 33

Met Thr Gly Gly Gly Ala Ala Leu Glu Thr Tyr Leu Glu Pro Leu Arg
1               5                   10                  15

Asp Ile Phe Ala Glu Glu Gly Val Asn Glu Ile Ser Ile Asn Asn Ser
            20                  25                  30

Cys Glu Val Trp Val Glu Asn Arg Gly Asn Ile Arg Cys Glu His Ile
        35                  40                  45

Ala Ala Leu Thr Thr Ser His Leu Arg Gly Leu Gly Arg Leu Ile Ala
    50                  55                  60

Gln Ala Thr Glu Gln Lys Leu Ser Glu Glu Thr Pro Leu Leu Ser Ala
65                  70                  75                  80

Ser Leu Pro Asn Gly Phe Arg Val Gln Val Val Phe Pro Pro Ala Cys
                85                  90                  95

Glu Gly Asp Lys Ile Val Met Ser Ile Arg Lys Pro Ser Ala Met Gln
            100                 105                 110

Leu Ser Leu Asp Asp Tyr Glu Lys Met Gly Ala Phe Ser His Val Ala
        115                 120                 125

Gln Gln Asn Asp Lys Leu Arg Asp Glu Asn Ser Glu Leu Gly Glu Leu
    130                 135                 140

Leu Ser Lys Gly Lys Ile Lys Glu Phe Leu Glu Thr Ala Val Gln Lys
145                 150                 155                 160

Lys Lys Asn Ile Ile Val Ser Gly Gly Thr Ser Thr Gly Lys Thr Thr
                165                 170                 175

Phe Thr Asn Ala Ala Leu Arg Ala Ile Pro Leu Glu Glu Arg Ile Ile
            180                 185                 190

Thr Val Glu Asp Ser Arg Glu Ile Val Leu Ser His Pro Asn Arg Val
        195                 200                 205

His Leu Leu Ala Ser Lys Gly Gly Gln Gly Arg Ala Arg Val Gly Thr
    210                 215                 220

Gln Asp Leu Ile Glu Ala Cys Leu Arg Leu Arg Pro Asp Arg Ile Ile
225                 230                 235                 240

Val Gly Glu Leu Arg Gly Ala Glu Ala Phe Ser Phe Leu Arg Ala Ile
                245                 250                 255

Asn Thr Gly His Pro Gly Ser Ile Ser Thr Leu His Ala Asp Thr Pro
            260                 265                 270

Arg Met Ala Ile Glu Gln Leu Lys Leu Met Val Ile Gln Ala Gly Thr
        275                 280                 285

Gly Leu Pro Ala Asp Gln Ile Val Asn Tyr Ile Met Asn Ile Val Asp
    290                 295                 300

Val Ile Val Gln Leu Lys Arg Ser Ser Gly Gly Val Arg His Val Ser
305                 310                 315                 320

Asp Ile Leu Phe Thr Lys Cys Ser Glu Gly Asn Lys
                325                 330
```